United States Patent [19]
Lester et al.

[11] Patent Number: 6,021,392
[45] Date of Patent: Feb. 1, 2000

[54] SYSTEM AND METHOD FOR DRUG MANAGEMENT

[75] Inventors: Douglas D. Lester, San Diego, Calif.; Salvatore Colella, New Kensington, Pa.; David D. Swenson, Encinitas, Calif.; Laird Broadfield; H. Thomas Daft, both of San Diego, Calif.

[73] Assignee: Pyxis Corporation, San Diego, Calif.

[21] Appl. No.: 08/986,384

[22] Filed: Dec. 8, 1997

Related U.S. Application Data

[63] Continuation-in-part of application No. 08/762,041, Dec. 9, 1996, and application No. 08/867,605, Jun. 2, 1997.

[51] Int. Cl.[7] .................................................. G06F 17/60
[52] U.S. Cl. .................................................................. 705/2
[58] Field of Search .............................. 705/2, 3, 22, 28; 235/375, 381, 385; 364/479.01, 479.11, 479.07, 479.06, 479.02, 479.14, 479.12; 221/2

[56] References Cited

U.S. PATENT DOCUMENTS

| | | | |
|---|---|---|---|
| 5,014,875 | 5/1991 | McLaughlin et al. | 221/2 |
| 5,460,294 | 10/1995 | Williams | 221/2 |
| 5,521,370 | 5/1996 | Hanson | 235/472 |
| 5,597,995 | 1/1997 | Williams et al. | 235/375 |
| 5,611,051 | 3/1997 | Pirelli | 705/28 |
| 5,682,728 | 11/1997 | DeBusk et al. | 705/29 |
| 5,713,485 | 2/1998 | Liff et al. | 221/2 |

*Primary Examiner*—Emanuel Todd Voeltz
*Assistant Examiner*—Thomas A. Dixon
*Attorney, Agent, or Firm*—Michael D. Steffensmeier; Donald O. Nickey

[57] ABSTRACT

A system is described in which a drug distribution center operates a computer software drug inventory management program in electronic communication with a health care provider computer software program for drug and health care supply distribution to patients. The system incorporates low unit dose measure drug and supply packaging including bar codes for automatically tracking drug information. The system further includes hand held drug information collection units for collecting the drug and supply information from the bar coded packages. The system provides complete drug and supply tracking from the drug supplier to a nursing station automated drug/supply dispensing machine.

51 Claims, 13 Drawing Sheets

Fig. 6

USER ID LABEL
Fig. 12
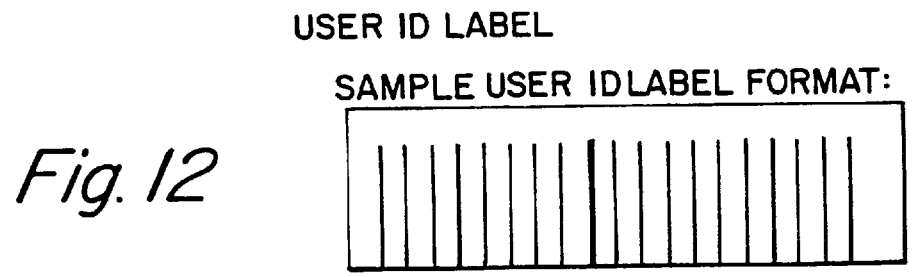
POCKET LABEL
Fig. 13
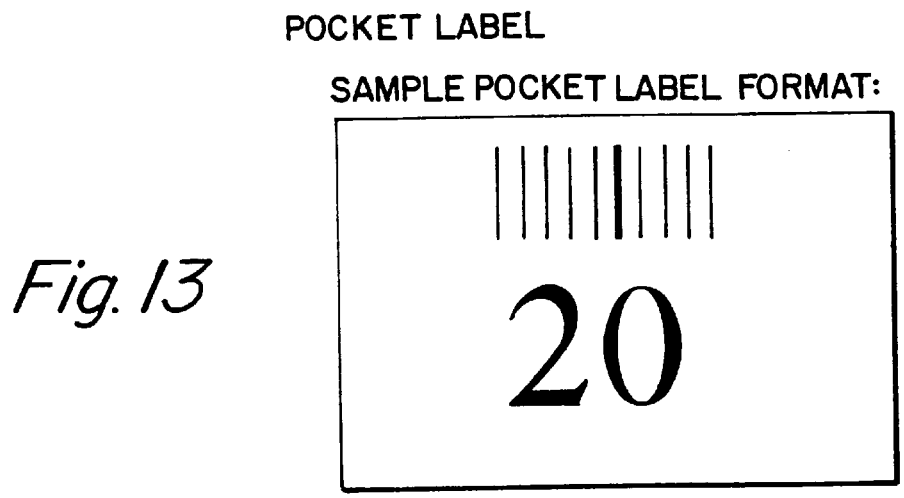
SHELF LABEL
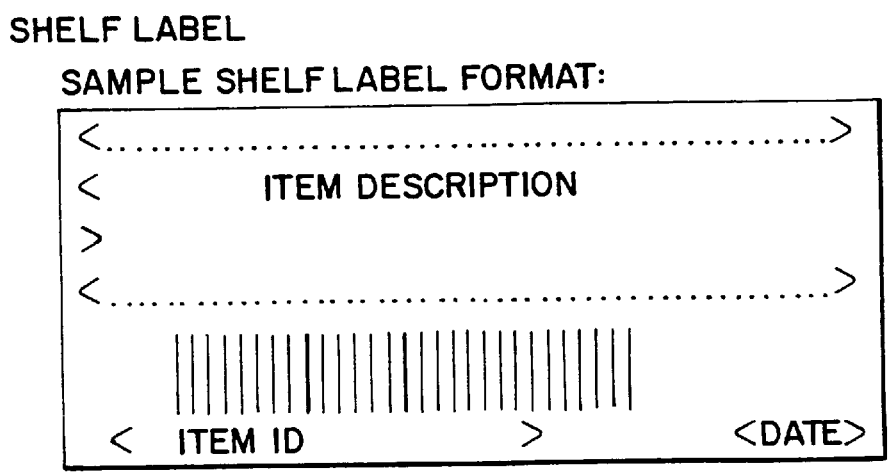
Fig. 14

SYSTEM AND METHOD FOR DRUG MANAGEMENT

RELATED APPLICATIONS

This application is a continuation-in-part application of pending application Ser. No. 08/762,041 filed on Dec. 9, 1996, entitled "System of Drug Distribution to Health Care Providers," and of pending application Ser. No. 08/867,605 filed on Jun. 2, 1997, entitled "System of Drug Distribution and Replenishment." These applications are incorporated herein by reference.

BACKGROUND AND SUMMARY OF THE INVENTION

The present invention relates generally to a system for drug and health care supply distribution and replenishment, and more particularly, the present invention relates to a system for drug information transfer, drug inventory management, and drug packaging, resulting in a unique system of drug distribution and replenishment.

It has been known for health care providers, such as hospitals, to have a pharmacist or pharmacy department within the hospital coordinate the dispensing of drugs to the patients of the health care institution. The pharmacists in such health care institutions have long been burdened with the increasingly complex record keeping and inventory management that results from hospitals caring for hundreds, if not thousands, of patients every day. Various methods have been employed to assist a hospital's pharmacist or pharmacy department with maintaining accurate records while attempting to reduce the burden of managing all of the information associated with drug distribution. The pharmacist's responsibility has included: filling individual patient prescriptions on a daily basis; maintaining sufficient inventory of each drug in order to have enough quantities of the drug in hospital stock to administer to patients on a daily basis; tracking of drug interactions to prevent a patient from being given a drug that has adverse affects when combined with other drugs; accounting for the purchase of drugs for use in the hospital; accounting associated with the giving of drugs to individual patients; distributing the drugs to the appropriate nursing stations within the hospital to suit each station's daily demands; tracking of drug expiration dates to rid inventories of expired drugs; and tracking of drug lot numbers, for example, in the event of a recall of a particular drug or drug lot number.

In recent years, hospitals have been assisted with drug distribution management by the introduction of drug dispensing machines, such as the machines described in some of Applicant's other patents, including U.S. Pat. No. 5,014,875, entitled "Medication Dispenser Station" and U.S. Pat. No. 5,460,294, entitled "Single Dose Pharmaceutical Dispenser Subassembly." Drug dispensing machines and health care supply dispensing machines have effectively created branches of the hospital pharmacy department at each nursing station where the dispensing machines are located. The dispensing machines are frequently arranged to be electronically connected to a central computer system within the pharmacy department for tracking drugs that were to be administered to patients in that particular patient care area of the hospital. In this manner, hospitals have improved the manner in which drugs are dispensed to patients and the record keeping required by the pharmacy department has been simplified somewhat by each patient care area electronically reporting the variety and quantities of drugs dispensed from each drug dispensing machine. Supply dispensing machines may also be able to electronically report the variety and quantities of supplies dispensed.

Health care providers, such as hospitals, have traditionally purchased drugs from drug distributors in bulk quantities (e.g., 100 single dose units of a particular variety of drug). Health care supplies may be purchased in a similar fashion and the scope of the present invention is meant to include health care supplies, as well as drugs. Although drugs will be discussed in more detail herein, this should not be interpreted to limit the broad scope of the present invention, which also includes supplies. While hospitals have purchased drugs in bulk due to manufacturer availability and being offered by the drug distributor, drugs are nevertheless dispensed at the health care institution on a patient-by-patient basis in low dose quantities. Therefore, hospitals have had to purchase and maintain large quantities of drugs until the drugs were eventually dispensed to the patients. Inventory turnover of drugs is usually measured in days, weeks or more. During such time, the hospitals have had to incur the associated expense of carrying this large inventory of drugs. Frequently, the result has been independent management of such large quantities, including unexplained loss of portions of the drugs in inventory, and even theft of portions of the inventory. In addition, the pharmacy department of the hospital has had the extra burden of tracking the drugs dispensed for patient use, as well as tracking the drugs that the pharmacy is carrying in its inventory. These issues also apply to health care supplies in health care institutions.

As the automated medication dispensing industry has matured, state regulatory agencies are beginning to address new technologies in the field and want assurance that an item in a pocket in a drug or medication dispensing machine is exactly what the machine represents it to be. Users of these drug dispensing machines also desire improvements in the refill and load procedures to make them more efficient.

The present invention is designed to overcome several of the above mentioned problems associated with health care provider drug and supply distribution. The present invention includes a unique form of drug packaging in combination with a computerized drug management software system. Low unit of measure quantities of a drug are packaged in an enclosure or package, such as a sealed plastic bag or a box, and the package is preferably marked with a lot number and a related lot number bar code for tracking the lot from which the drugs within that particular package originated. The package may also include an expiration date and related expiration date bar code for tracking the expiration date of the drugs within the package. The package may also include an NDC number and related NDC (Motional Drug Code) number bar code for identifying the variety of drug packaged within the enclosure. The package and bar code on the package may also include further information regarding its contents.

Once the drugs are packaged, they may be warehoused at a drug distribution center. When a health care provider requires drugs, the drug distribution center delivers the low unit measure packages in accordance with the hospital's current needs. Once the low unit measure packages arrive at the hospital, the bar codes may be scanned by the hospital pharmacy and/or scanned at the appropriate drug dispensing machine in the hospital to be automatically logged into the hospital's drug information management system in electronic communication with the drug distributor's management information system to track exactly what drugs and quantities arrived at the hospital in each shipment. Furthermore, the bar codes on the packages may be used to track the drugs that are placed in each drug dispensing machine at each patient care area within the hospital. The hospital's drug management information system will thus contain information about the items placed in each drug dispensing machine in the hospital, including drug type, lot numbers, expiration dates, and the like.

The present invention incorporates new features and components to improve existing automated drug and supply dispensing systems as well as potentially change existing operations in the pharmacy. The bar coded packages are designed to work with the latest machines and systems going to the field and might be used for legacy machines and systems currently in the field. One goal of the present invention is to standardize the machine replenishment procedure of items (drugs, supplies, etc.) so that the process of putting away items in a machine is the same regardless of whether the items came from the in-house pharmacy or from a distributor outside of the hospital.

In addition, the present invention provides a computerized electronic interface between the hospital software system that tracks the drug distribution within the hospital and the drug distributor's software system at the drug distribution center warehouse. By enabling these two systems to communicate with each other, the system of the present invention provides a complete drug distribution management system from the warehouse to the patient care area within the hospital.

The system of the present invention is for drug and health care supply distribution and replenishment. The present invention includes a package containing at least one drug and the package has information thereon relative to the drug. This information is preferably in bar code form. It has a computer at a health care provider and the computer is adapted for storing said drug information and maintaining drug counts. There is one or more automated drug dispensing machines at a location at the health care provider and the automated drug dispensing machines are in electronic communication with the computer. The present invention also includes one or more drug information collection units (preferably hand held units) that are adapted to obtain drug information from the package by scanning the bar code and the drug information collection units are adapted to communicate the drug information to the computer. The system of the present invention, including the computer, the automated drug dispensing machines, and the drug information collection units, records drugs received by the health care provider, records drugs dispensed to patients at the health care provider, and records an ongoing inventory of drugs stored at the health care provider.

The present invention may also include a second computer located at a drug supplier facility, with the second computer in electronic communication with the first computer, and the second computer being adapted to receive an electronic purchase order from the first computer. The system of the present invention preferably includes an electronic interface, such as an interface computer, between the first computer and the second computer to enable the first computer and the second computer to electronically communicate and share data with each other.

Various objects and advantages of the present invention will become apparent from the following detailed description when viewed in conjunction with the accompanying drawings, which set forth certain embodiments of the invention.

BRIEF DESCRIPTION OF THE DRAWINGS

FIG. 6 shows an example data screen of a preferred form of the computer software system of the present invention.

FIG. 12 shows an example of a user ID label in accordance with the present invention.

FIG. 13 shows an example of a pocket label in accordance with the present invention.

FIG. 14 shows an example of a shelf label in accordance with the present invention.

DETAILED DESCRIPTION OF PREFERRED EMBODIMENT(S)

Figure 1A:
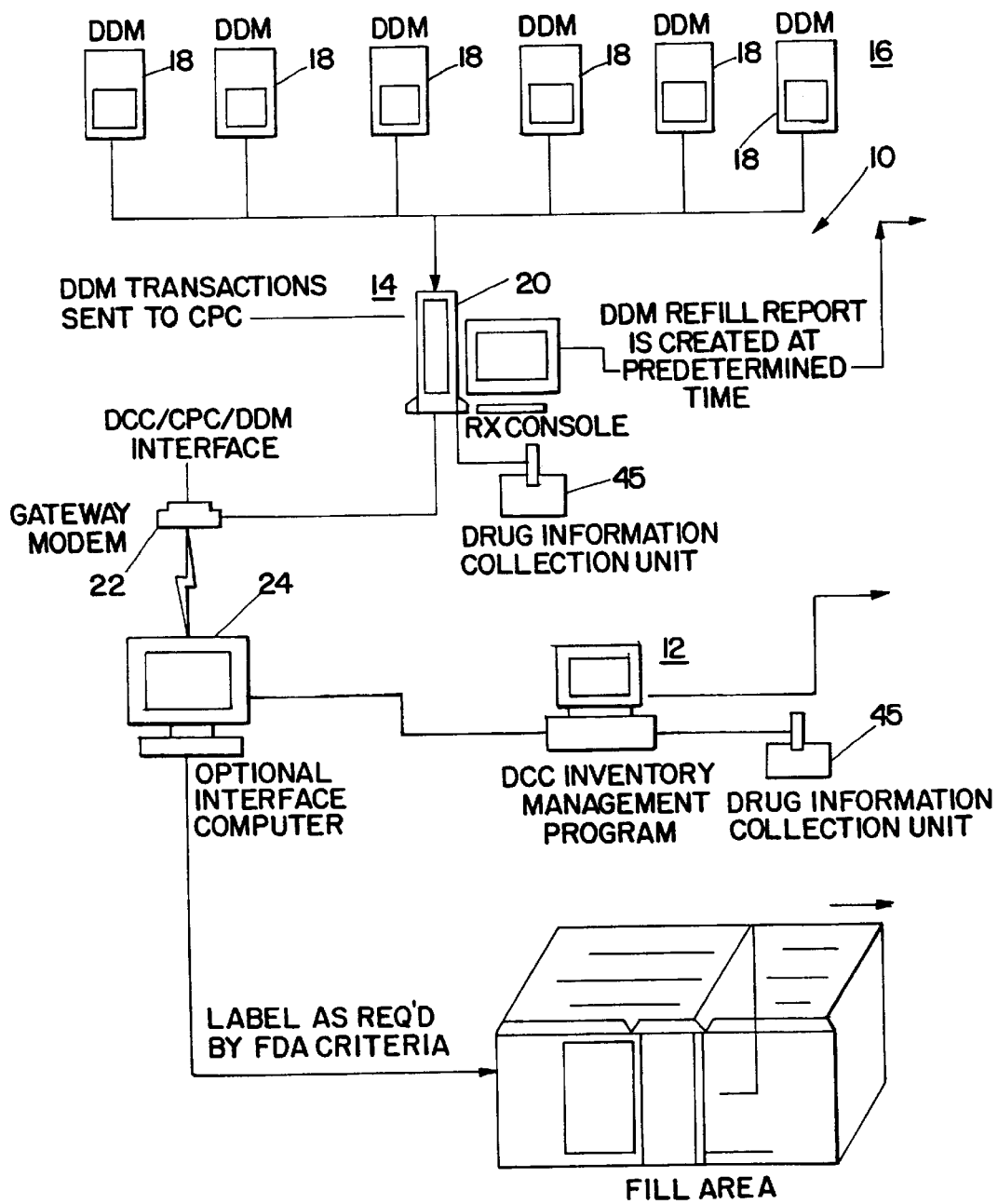
FIGS. 1A and 1B show a schematic diagram of a preferred embodiment of the system of the present invention.
Figure 1B:
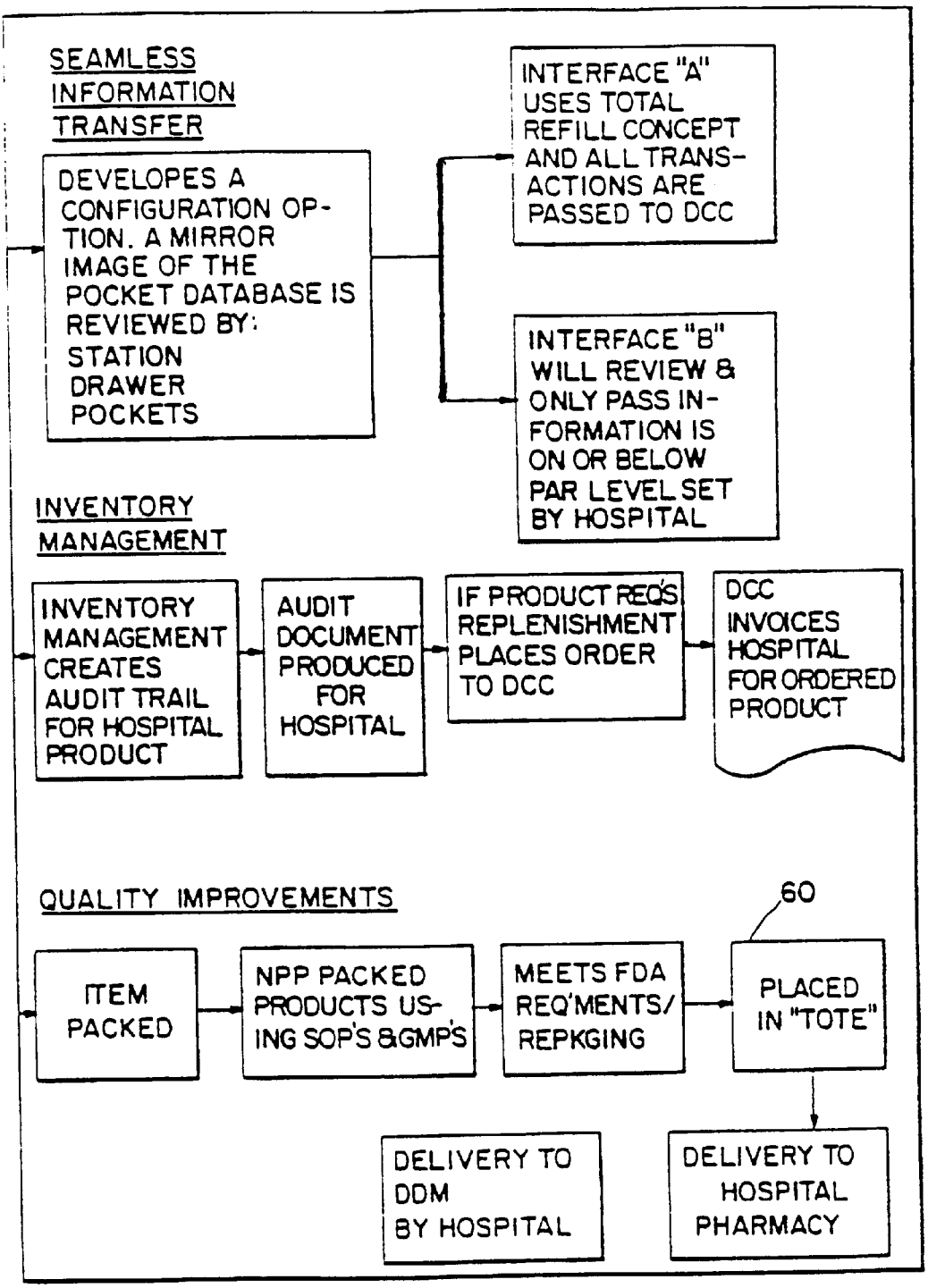

The drug and health supply distribution and replenishment system 10 and its component parts of the preferred embodiments of the present invention are shown in FIGS. 1 through 14. Referring now to the drawings, and particularly FIG. 1A, a preferred embodiment of the system of the present invention is shown. The system shown at 10 may typically have at least three areas of data tracking of drug or supply distribution. A first area 12 is the drug distribution center which is usually at a remote site from the health care provider institution. At the drug distribution center or at a computer facility in association with the drug distribution center, the first software program may be installed on a personal computer or network server for facilitating d rug distribution management of low unit dose measures of the present invention. As used herein, low unit dose measures include single dose measures of drugs and/supplies.

A second drug distribution management software program of the present invention is installed at the health care provider facility 14 (for example, in the pharmacy department or another area of a hospital) or at a computer facility in association with the health care provider. This second software program may be the same program as the first software program with each program handling the appropriate information at its location. A third area of the present invention is at the various nursing stations 16 within the health care facility, primarily at drug dispensing machines ("DDMs") 18 located at nursing stations. In one embodiment, the second drug distribution management software may be installed at the nursing stations. The DDMs 18 are located conveniently near the nursing activity and, depending on the department, a DDM 18 may be closer to the patient bedside than to the nursing station.

In its preferred form, the present invention includes electronic communication and data sharing between the drug distribution software program and the health care provider software program, as well as between the drug dispensing machine software program and the health care provider software program. In another embodiment, there may be data sharing and communication between the drug dispensing machine software program and the drug distribution software program. The communication between the DDMs 18 and the health care provider's pharmacy software program of the present invention, may be accomplished through hard wiring the drug dispensing machines throughout the facility to a central computer 20 operating the pharmacy second software program. Other suitable means, such as RF communication, to provide a communications link between the drug dispensing machines and the health care provider's pharmacy software program may also be used. Communication between the drug distribution center program of the present invention and the health care provider software program of the present invention may be accomplished via modem 22 and interface software running at each site as further described below. The interface may be, for example, a UNIX gateway. Since the distribution center may serve more than one health care provider in its region, each health care provider would be equipped to access the distribution center computer system. This may involve having a gateway at the health care provider and another at the distribution center for gateway to gateway communication. Various other ways of setting up the communication link between the health care provider and the distribution center would be apparent to those of ordinary skill in the art when made aware of the contents of the present specification.

In accordance with a preferred embodiment of the present invention, a number of drug dispensing machines 18 within a health care facility 14 are in communication with the health care facility's central pharmacy computer ("CPC") 20, which is running the drug inventory management software program ("DIMS") of the present invention. Each DDM 18 may be uniquely identified by an identification code stored in the memory of the CPC 20. This memory may be any suitable memory including hard disk, jazz drive, tapes, etc. The DDM's identification code preferably includes information about the DDM's 18 physical location within the health care facility. Each DDM 18 may have a plurality of drawers, compartments, doors, bins, shelves, take/put buttons, coil dispensers, and/or pockets within each drawer, for storing and dispensing certain drugs for later administering to patients. The DDMs 18 may also be supply dispensing machines.

The CPC 20 may be a computer or collection of computers that comprise the center of control for the DDM 18 system. The CPC 20 is the master database, time goal, report generating, configuration and management piece for the system. The interface computer 24 communicates with external systems (such as software at DCC 12). In another embodiment, the interface computer 199 (FIG. 9) communicates with external systems (such as software at DCC 12) and devices (the cradle 165 in FIG. 10 which facilitates communication between the interface computer 199 and the drug information collection units. As used herein, interface computers 24 and 199 may refer to the same computer. Interface computer 199 is preferably separate from the CPC 20 in order to isolate processing overhead of communicating with a number of other systems. Interface computer 199 gets from the CPC 20 a copy of messages related to DDM activity from which it builds a database of system inventory. This database is the source of information for picking/checking reports related to drug replenishment activity, order information to the distribution center or vendor, and picking data upon which the hand held drug information collection unit's 45 work.

In a preferred embodiment, the CPC 20 communicates via network or serial communication to the interface computer 199. The interface computer 199 communicates by serial communication to the drug information collection unit 45 via the cradle interface 165. Interface to a vendor is accomplished in several ways. A company may have its software program on a machine resident at the customer's site. Communication between interface computer 199 and the company's resident software program is done point-to-point on the local network. The software program then communicates to the distribution center via modem. With other vendors, a direct modem link may be made from the interface computer 199 directly to the vendor's distribution center or data center.

The pharmacist may arrange to stock each DDM 18 with particular drugs and/or supplies in particular drawers and compartments as well as in particular pockets within each drawer. Each DDM 18 preferably includes data entry means such as a keypad or touchscreen to enable nursing staff to enter the time when a particular drug is administered to a patient, what drug was administered, what quantity was administered, and to which patient. Once entered into the DDM 18, this information is preferably automatically received by the CPC 20 and utilized in DIMS running at the health care facility CPC 20. In another embodiment, the DDM 18 can also send this information directly to the DCC 12 (as well as to the CPC 20). The transaction time is derived from the system transparently to the nurse doing the transaction. This is considered to be the vend time for administration. In a preferred embodiment, this vend time, administration time, and related information is captured by the DDM 18 and the CPC 20.

Once the CPC 20 receives the drug administering information from the plurality of DDMs 18, this information may be sent by the CPC 20 to the drug distribution center computer ("DCC") 12 also running a version of DIMS. It is important to note at this point that the DIMS running at the DCC 12 and the DIMS running at the CPC 20 may be the same program installed at multiple sites or it may be two separate programs adapted to communicate with each other. In either case, the CPC DIMS is adapted to track quantities and varieties of drugs received and administered to patients, and the DCC DIMS is adapted to track quantities and varieties of drugs shipped to particular health care providers and the remaining drugs those health care providers have purchased but which have not yet been requested for shipment to the health care facility. The DCC DIMS is also preferably adapted to produce an invoice to the health care provider for bulk drug purchases. The DIMS is preferably a Windows based program.

The software DIMS of the present invention is adapted to account for low unit dose measures of drugs. Unlike the drug distribution systems of old which accounted for bulk purchases but offered little or no low unit dose tracking, the present invention is especially designed to enable health care providers to reduce their own inventory of drugs and supplies and shift inventory management responsibilities to the drug distribution center or the supply distribution center. In this manner, the health care facility only receives those drugs that it will use in a relatively short period of time, thus substantially reducing inventory management responsibilities at the health care facility. Each health care facility would establish its own comfort level of drugs on hand and order from the drug distribution center accordingly. With the electronic communication between the DDMs 18 and the CPC 20, the health care facility would have daily (or more frequently if desired) reports of drugs on hand at each DDM 18.

It should also be noted here that both the CPC 20 and the DCC 12 roles could be outsourced to third parties in whole or in part, and still accomplish the intended purpose of the present invention. Furthermore, various programs may be written in various computer languages and formats to accomplish the roles of the CPC, DCC, and DDM data processors. Those specific programs, hardware and components described herein are not to be interpreted as limiting the broad scope of the present invention.

Another unique aspect of the present invention is the manner in which the low unit dose quantities of the drugs are packaged for delivery to each health care facility. In one embodiment of the present invention, a small plastic bag 30 is used as a package for unit dose measures of a drug. The individual doses of the drug may be contained in blister packs and placed in the plastic bag 30 in predetermined quantities. The plastic bag 30 and the unit doses of drugs may then be sealed with a perforated edge for later easy opening by health care providers. The plastic bag 30 may be readily placed within the drawers, compartment, pockets, etc. of a DDM 18. Besides plastic bags 30, other suitable packaging may be used for delivery to each health care facility, including boxes, cards of blister packs, blister packs stapled or otherwise connected or bundled together, and the like. The plastic bags 30 and other suitable packages are generally referred to herein as package 30.

Figure 2:
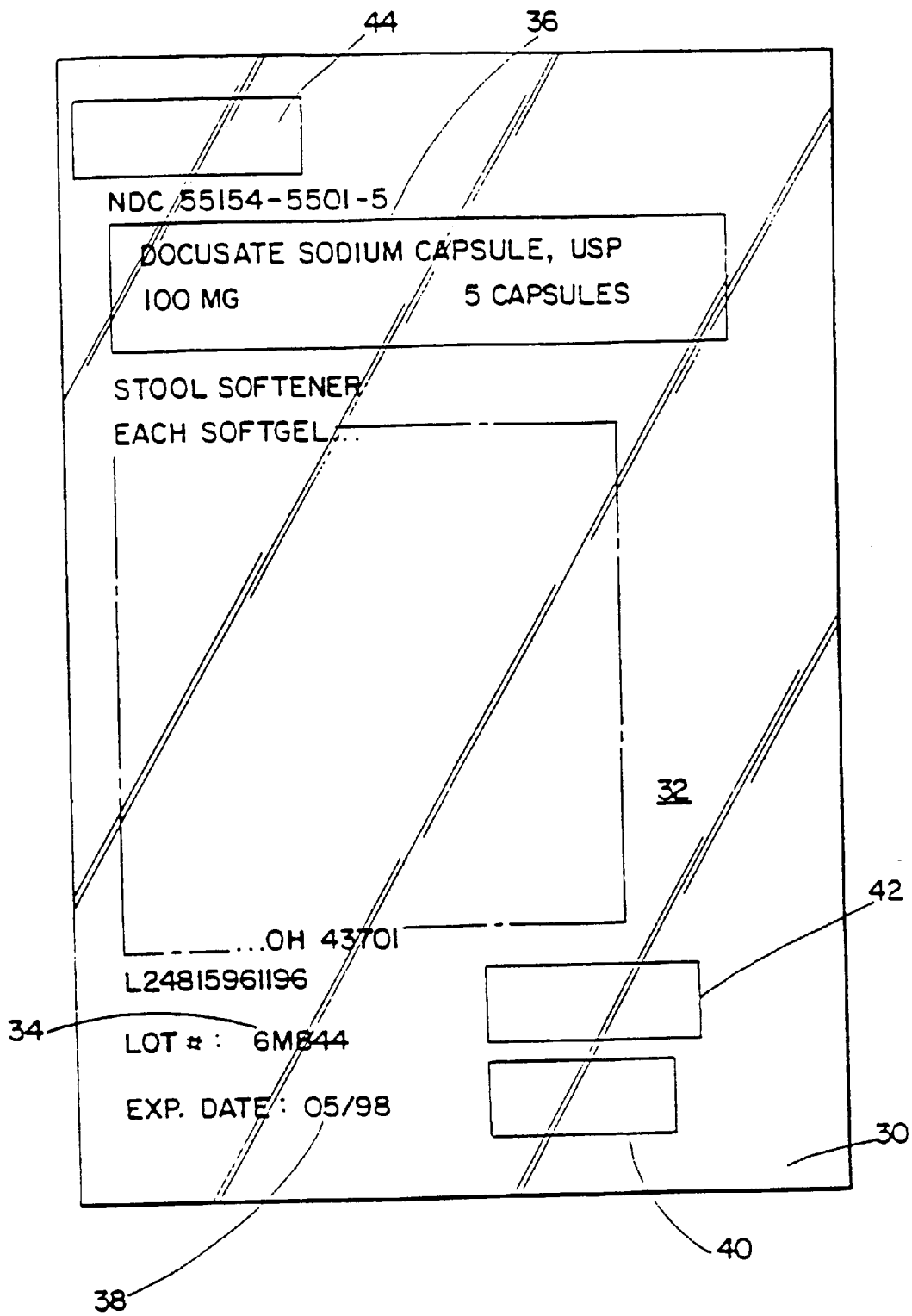
FIG. 2 shows an actual size of a face of a plastic bag for low unit measure drug packaging of one embodiment of the system of the present invention.
Figure 3A:
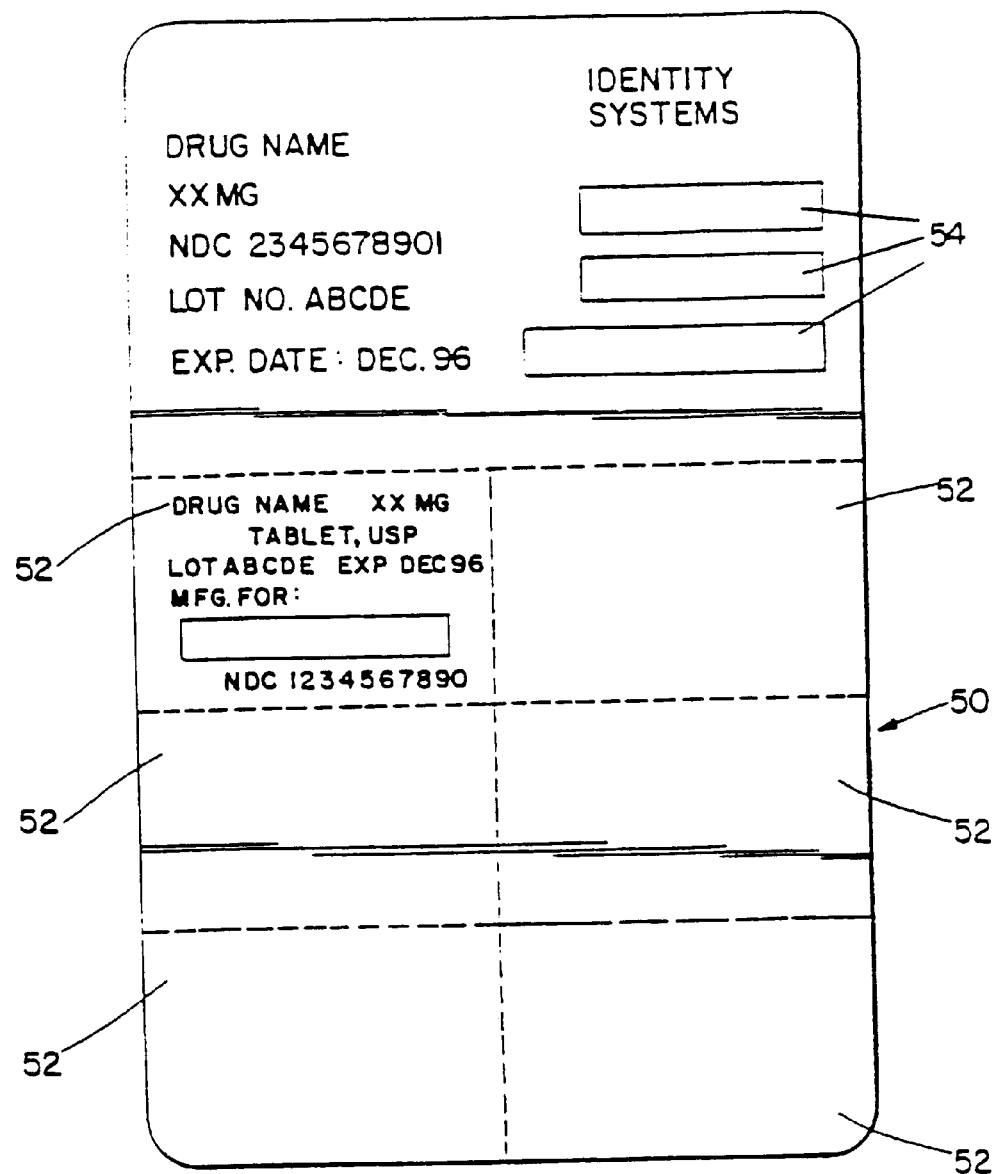
FIG. 3A shows an actual size of a face of a drug packaging card for low unit dose drug packaging of another embodiment of packaging for the system of the present invention.

As shown in FIGS. 2 and 3, prior to placing a drug in a package 30 as described above, the package 30 may be printed on a face 32 thereof, with certain FDA required information, NDC, and other information. For example, the drug manufacturer's lot number 34, the variety of the drug 36, and the expiration date 38 of the drug may be printed or otherwise placed on the package 30. The NDC is used to identify the item in the package 30. In addition, in a preferred embodiment of the present invention, certain of this information may be printed on the package 30 in the form of bar codes. With the use of bar codes there is less chance of human data entry errors when compared to manual data entry. Also, bar codes are faster to scan and thus enter the information into the DCC 12, CPC 20 and DDM 18. Two-dimensional bar codes may be preferable because they can contain more information in the same amount of space as one-dimensional bar codes. The bar coding may be accomplished by commercially available bar coding equipment.

Using for example a low unit dose package 30 containing a bar code 40 that includes the expiration date of the drug in accordance with the present invention, the system 10 of the present invention offers a relatively fast and efficient system for tracking drugs that need to be removed from the DDMs 18. If a drug has expired, the CPC 20 may inquire about the expiration dates of all of the drugs within a DDM 18 (which in accordance with the present invention were earlier scanned and entered into the DDM 18). If expired drugs are shown to be present, the CPC 20 will know exactly which DDM 18 contains the expired drugs by referring to the DDM identification code. The CPC 20 and the particular DDM 18 will also know exactly which drawer, and pocket within that drawer, contains the expired drugs. In a preferred embodiment, when prompted by a user, the appropriate drawer will pop open and the appropriate pocket will be identified on the computer screen of the DDM 18, by a light or an LED in or by the pocket, or by other suitable means to enable a user to quickly find the correct pocket. Thus, tracking of expired drugs for removal is handled electronically rather than the user having to manually check each drawer of each DDM 18. Likewise, lot numbers 42 and drug identification information 44, as well as other information may be placed on the package 30 in bar code form. Drug information collection units 45, such as bar code scanners, may be located at each site 12, 14, 16 to make the system 10 highly accurate and efficient. These drug information collection units 45 are preferably hand held units.

Figure 3B:
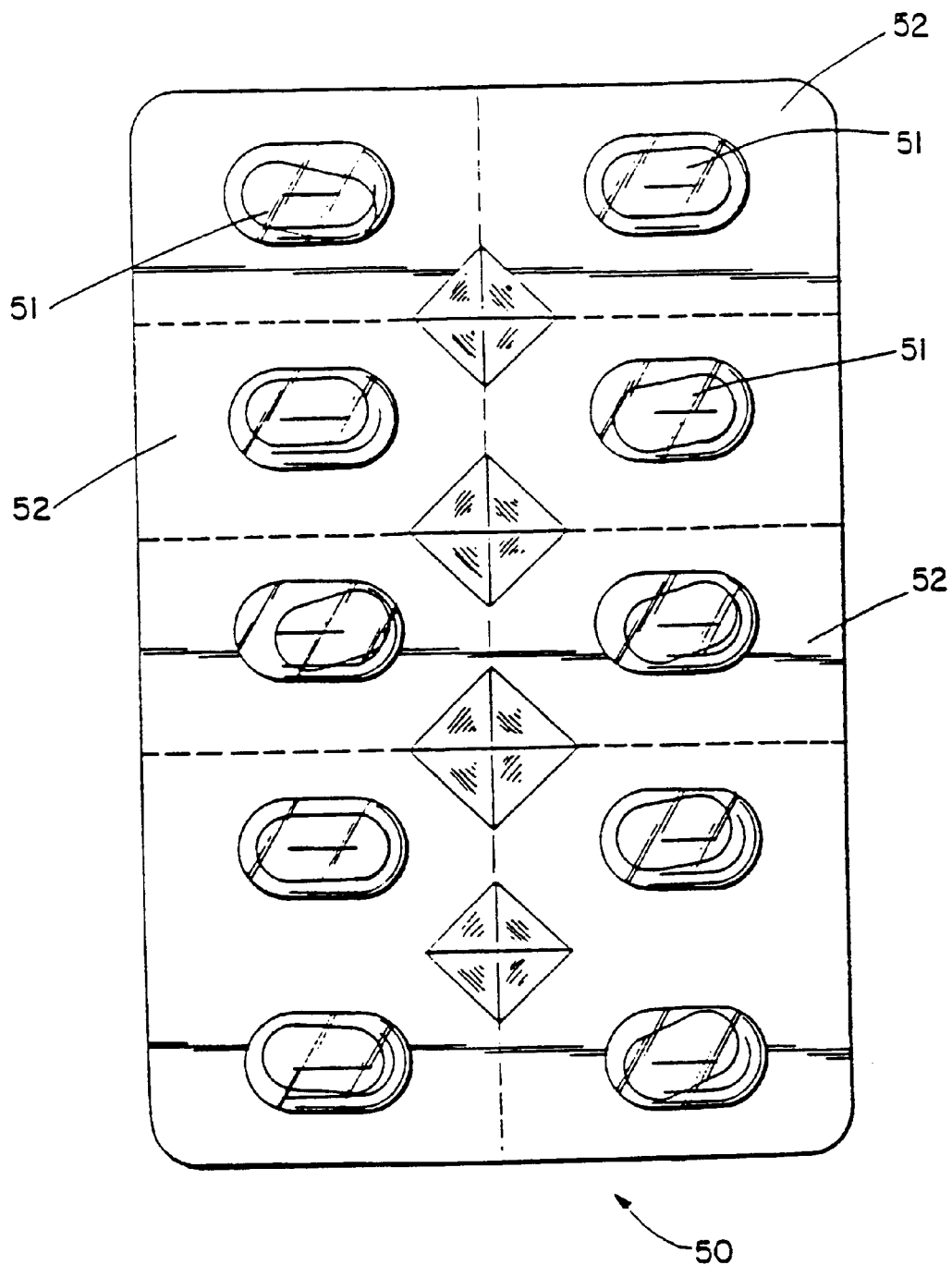
FIG. 3B shows an opposing side of the drug packaging card of FIG. 3A.

In another embodiment of the present invention, a small paperboard card 50 serves as the drug package for low unit dose measures. The card 50 is preferably of a size that enables it to be placed in a pocket of a drawer of a DDM 18. The card 50 may contain unit doses 51 of drugs in separate blister packs 52 attached to the card 50 at perforated seams as shown in FIG. 3B. The card 50 and/or each blister pack within the perforated seams may also contain bar coded information 54 as explained above.

In accordance with a preferred embodiment of the present invention, the CPC 20 generates an electronic purchase order that is sent to the DCC 12. The purchase order contains a request for a bulk purchase of one or more varieties of drugs and also may include a request that only a certain lesser quantity than ordered be delivered at the present time. The DCC 12 acknowledges the purchase order and fills the requested order. The DCC 12 also tracks what quantities of the drugs ordered remain in inventory at the distribution center awaiting shipment upon request by the CPC 20. The DCC 12 produces an invoice for the bulk order and sends the invoice to the CPC 20.

In a preferred embodiment, the distribution center ships the requested unit dose packages of drugs in "totes" (shipping containers, bags, boxes or other suitable containers) 60 which are predesignated for a particular DDM 18 at the health care facility. Therefore, instead of the health care facility having to spend resources on getting the right drugs to the right DDM 18, the DCC 12 can accomplish this in a much faster manner through its tracking of data received from the CPC 20 (which received its data, in part, from each DDM 18) and the subsequent shipping of pre-designated and properly labeled totes 60. The outside of each tote 60 may also contain bar code information for easy tracking of totes 60 as they are sent from the distribution center and received at the health care facility.

Figure 4:
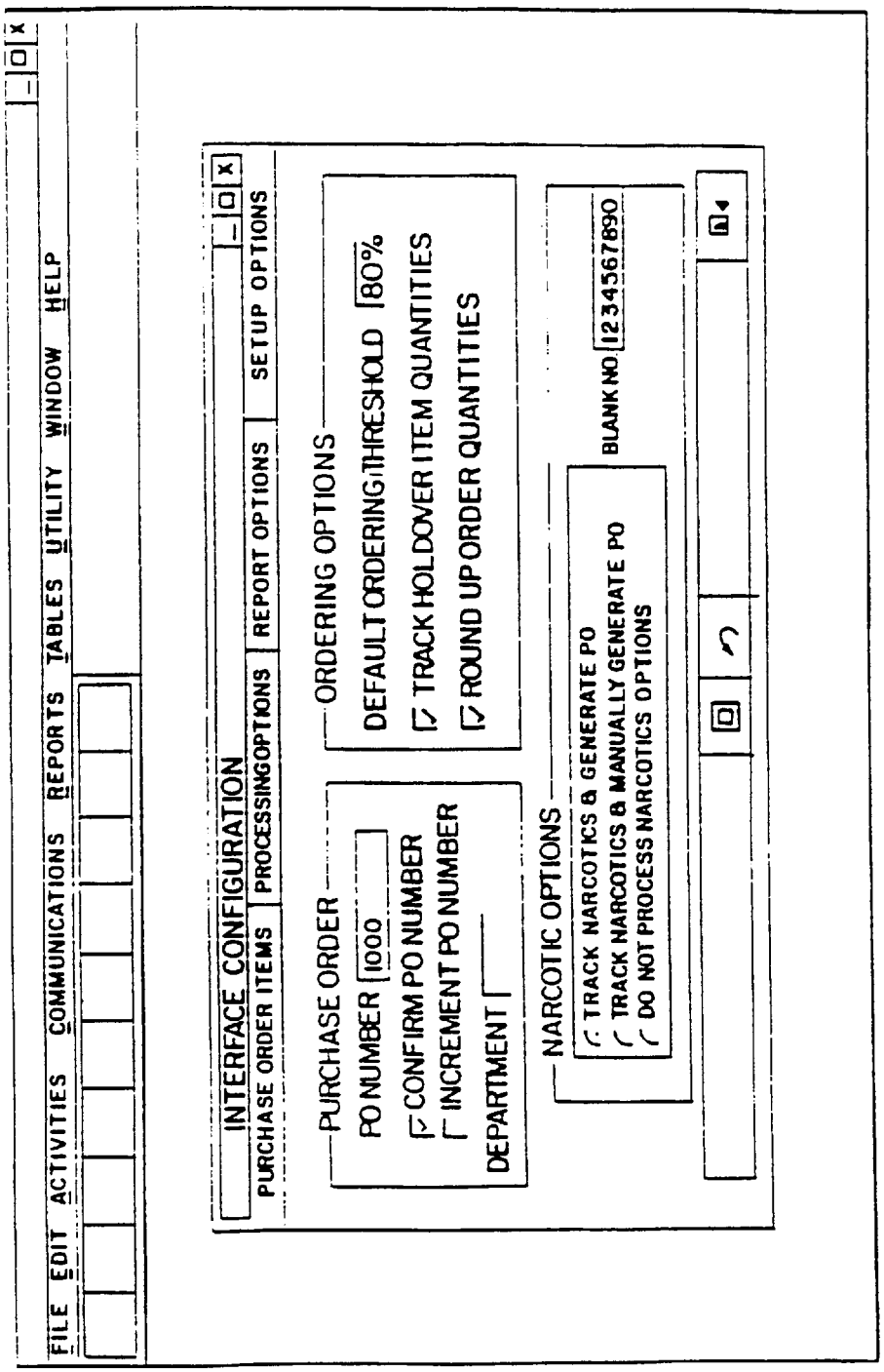
FIG. 4 shows an example of a preferred processing interface configuration of the computer software system of the present invention.
Figure 5:
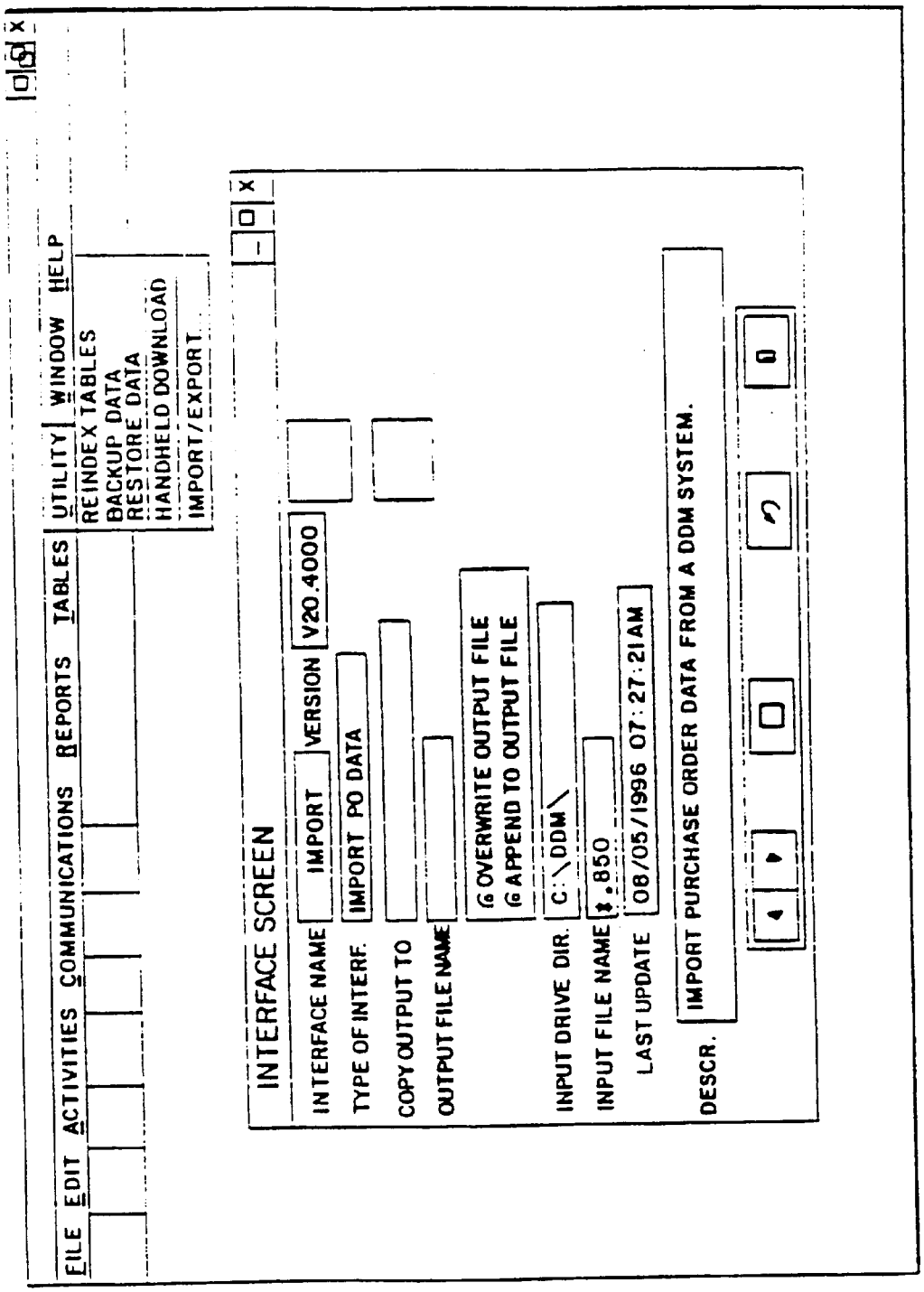
FIG. 5 shows an example of a data interface screen of a preferred form of the computer software system of the present invention.
Figure 6:
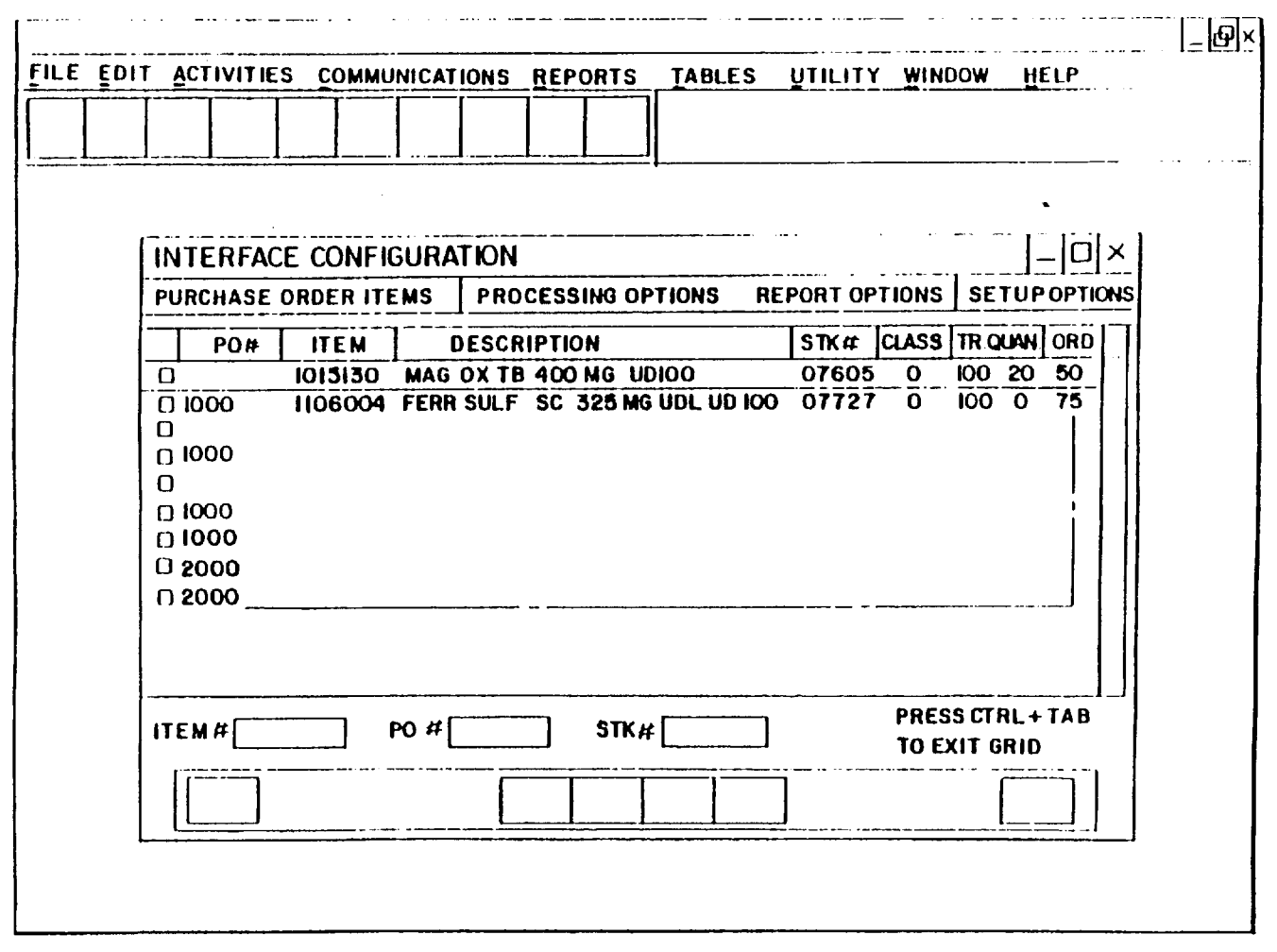

Example of CPC, DCC and DDM Software
Configuration and Operation Steps for Interfacing
(see FIGS. 4–6 showing examples of an interface configuration, a data interface screen, and a data screen of the computer software system):

1. Confirm that DDM system is set up with the CPC 20 and in communication with the DCC 12. Within the DDM system, the interface may be configured with the following settings:
 a. Set to Stockless—ordering information is broken down at the item level per DDM 18.
 b. Set to Usage Net Vends—ordering quantities are based on the amount dispensed since the last time PO generated.
2. Match the DDM numbers used to identify items with the corresponding DCC item numbers.

3. Load either the DDM item numbers into the DCC 12 or load the DCC item numbers into DDM 18.
Steps:
1. Access the interface from the Import/Export option located off the utility menu in DCC 12.
2. If more than one interface is installed, operator may need to click on the next or previous arrows in order to locate the DDM interface.
3. Select the DDM interface as depicted below:
4. Specify the location of the incoming files. To specify the drive and directory where the incoming file(s) resides, click the mouse on "Input Drive/Directory" and a screen will come up allowing operator to select a path. Or operator may type in the desired drive and directory. If operator does not specify an incoming path, the interface defaults to searching for incoming files in the DCC system directory. If none are found, the interface will terminate processing.
5. "Input File Name" may be set to—*.850
6. Save changes by clicking on the save button (disk icon).
7. To configure the interface, click on the configuration button (wrench icon) and this brings up the following screen:

Purchase Order Items

This screen will be explained within the "Running the Interface" section of this guide. To continue with the setup and configuration, click the Processing Options tab.

Processing Options

Initially, fields set with default system settings.
1. Purchase Order Settings
PO Number—This is the purchase order number assigned to the incoming DDM order. The purchase order number may be 12 alphanumeric characters.

Confirm PO Number—If selected, the following screen will be displayed before an order is created within the DCC 12 system for each incoming DDM order. The screen displays the purchase order number that will be associated with the incoming DDM order.

Confirm whether or not operator wants to use this purchase order number. Operator may reset the number by typing in a new one and then select continue (rocket icon). The newly entered purchase order number is assigned to the incoming DDM order.

Increment PO Number—If selected, the purchase order number will automatically be incremented during processing. Once selected, specify the incremental value for the purchase orders.

Department—Enter the department code associated with the items on the incoming DDM order. This department code may be associated with all items on the order. Leave blank if operator does not want to assign a department code to the ordered items.

Ordering Options

Default Ordering Threshold—Percent of ordering unit met before item is ordered. This field sets the ordering level for all items. The ordering threshold must be met or exceeded for an item to be ordered. For example, if the threshold is set at 80% for a 100 count bottle of Tylenol, the interface will not place an order until at least 80 tablets have been requested from the DDM system. The ordering threshold value may be stored in the UDF2 field within Item Maintenance.

Track Holdover Item Quantities—By activating this field, the interface will carry over the extra quantity of a particular item or the quantity of an item that did not meet the ordering threshold and use it when calculating the next purchase order quantity.

Continuing from the above example, say only 80 Tylenol tablets were requested from the DDM 18. However, the hospital was shipped a 100 count bottle. The hospital received twenty additional tablets. The interface will track the additional tablets, and when the next request for that particular Tylenol comes through, the interface will subtract the 20 tablets from the requested amount. It is this adjusted value that will be compared to the ordering threshold.

Another scenario where this setting comes into play occurs when the Tylenol order is for 20 tablets. This does not meet the ordering threshold, so the item is not ordered. These 20 tablets will carry over and be added to the next request for Tylenol.

If this field is not activated, the carry over quantities are not tracked and each request is evaluated on an individual basis. It is recommended to activate this option.

Round Up Order Quantities—Round calculations up to the next ordering unit. For example, if activated and an order for 135 Tylenol tablets comes across, the interface would order two 100 count bottles.

Narcotic Options

Select One Option

Track Narcotics & Generate PO—The interface will generate a purchase order for narcotic items that are ordered by the DDM system. If selected, enter the Blank Number in the available space.

Track Narcotics & Manually Generate PO—The ordered quantities for narcotic items will be tracked within the interface, but a purchase order will not automatically be generated for these items. These items will be tracked until a purchase order for narcotic items is manually requested. There is a mechanism for generating this purchase order on the Purchase Order Items screen. The "Running the Interface" section offers manually triggering a purchase order for narcotic items.

Do Not Process Narcotic Items—All orders for narcotic items are ignored by the interfaces. Ordering narcotic items for the DDM system is handled outside this interface. To save changes click on the save button (disk icon). Continue with the setup and configuration by clicking the Report Option tab.

Report Options

Report Setting

Print Order Exception Report when processing order—If activated, the Order Exception Report will automatically be generated and printed, if appropriate, while the incoming DDM order is being processed. Continue with the setup and configuration by clicking the Setup Options tab.

Setup Options

I. Cross-Reference Method

Denote whether DCC item numbers are matched up and stored in the DDM alternate ID field for all items, or whether the DDM item numbers are matched up with their corresponding DCC item numbers and stored within the DCC 12 system.

If DDM item numbers are stored in DCC 12, the following will be displayed.

II. DDM Item # Found In

Identify in which field the DDM item numbers are stored within the DCC 12 system. Both the "Stock Number" and the "UDF1" fields are accessible through Item Maintenance. At this point setup and configuration are complete, and the system is ready to import purchase orders from the DDM system.

Running the Interface

Steps:
1. The interface is run from the Import/Export option located off the utility menu in the DCC 12.
2. Select the DDM interface.

3. Adjust "Input Drive/Directory" as needed.

4. Save changes by clicking on the save button (disk icon).

5. To execute the interface, click on the launch button (rocket icon). The DDM order will be imported into the DCC 12. The interface will accumulate the item quantities across DDMs 18 into one purchase order. If there are multiple purchase order files from the DDM 18, all items and order quantities will be consolidated into one purchase order within the DCC 12.

6. The interface will notify operator upon completion.

7. When processing has finished, review the incoming order within the Purchase Order section of DCC 12.

8. Also, there is a separate screen within the configuration portion of the interface for reviewing purchase order items and for tracking carry over quantities. This is accessed from the main DDM interface screen. To bring it up, click on the configuration button (wrench icon). The following screen appears:

Purchase Order Items

I. Item Grid

All items that have been ordered through the DDM system are listed. The main purpose of this grid is to allow review, and if necessary, adjustments to the carryover quantity and ordering threshold for a particular item.

Columns:

PO #*—the last purchase order that this item appeared on. If blank, the item was not ordered during the most recent processing or there is overstock of that particular item which keeps it from being reordered.

Item #*—DCC's item number for this product.

Description*—the trade name of the item as identified by the manufacturer.

Stock #*—the corresponding DDM item number for this product.

Class*—narcotic classification

UOIF*—Unit Of Issue Factor—the number of units in the packaged product. Can be edited within Item Maintenance to reflect the number of unit doses contained within the package.

Track Qty—this is the carry over quantity associated with the item. A negative value represents overstock and that amount needs to be deducted before an order is placed. A positive value is the ordering quantity that has been accumulated to this point for the item. This value will be added to subsequent orders and compared against the ordering threshold. This column is highlighted because the value can be edited. Adjustments can be made to this field as deemed necessary.

Ord %—the ordering threshold associated with that particular item. This column is highlighted because the value can be edited. Adjustments can be made to this field as deemed necessary.

*—Fields can not be edited in normal browse mode. Only Item # and Stock # can be edited in ADD mode (plus icon).

II. Additional Features

Exception Override—there is capability to override an exception item status and order that item. In other words, if an item did not meet the ordering threshold, select that item and generate a purchase order for it.

Steps:

1. Tag the desired exception item(s). This can be accomplished two ways. One way is to select each item individually. Do this by marking the first column (*) with either the mouse or by hitting the space bar. The other manner for selecting exception items is to use the "Tag Exception Items for Order" option. Click the option button (check box icon). A list of options will appear. Select the "Tag Exception Items for Order" option and all exception items will be selected for the purchase order. Deselect an item by clicking on the selected check.

2. Select the launch button (rocket icon) to create a purchase order with the selected exception items.

3. Review the purchase order within DCC 12.

Adding Items—operator may add items individually to the table. Choose to do this if operator wants to preset the item with a unique threshold or tracking quantity.

Steps:

1. Click on the add button (plus icon) from the toolbar.

2. Fill in the appropriate data: DCC item number, stock number, track quantity, and threshold.

3. Click on the save button (disk icon) to save addition.

Narcotic Ordering—This feature is meant to be used in conjunction with the "Track Narcotics & Manually Generate PO" processing option. Order quantities have been tracked within the interface. When ready, operator may create a purchase order for the narcotic items.

Steps:

1. Tag the desired narcotic item(s). This can be accomplished two ways. One way is to select each item individually. Do this by marking the first column (*) with either the mouse or by hitting the space bar. The other manner for selecting exception items is to use the "Tag Narcotic Items for Order" option. Click the option button (check box icon). A list of options will appear. Select the "Tag Narcotic Items for Order" option and all narcotic items will be selected for the purchase order. Deselect an item by clicking on the selected check.

2. Select the launch button (rocket icon) to create a purchase order with the selected narcotic items.

3. Review the purchase order within DCC 12.

III. Screen Commands

* Search—search for a specific item number, purchase order number, or stock number by typing in the desired number within the space provided. The area to enter the search values can be found above the command buttons.

* Use the Tab key and/or the mouse to maneuver on the screen.

* To exit the interface configuration, click on the exit button (exit door icon).

• To delete an item record, click on the delete button (garbage can icon).

Figure 7:
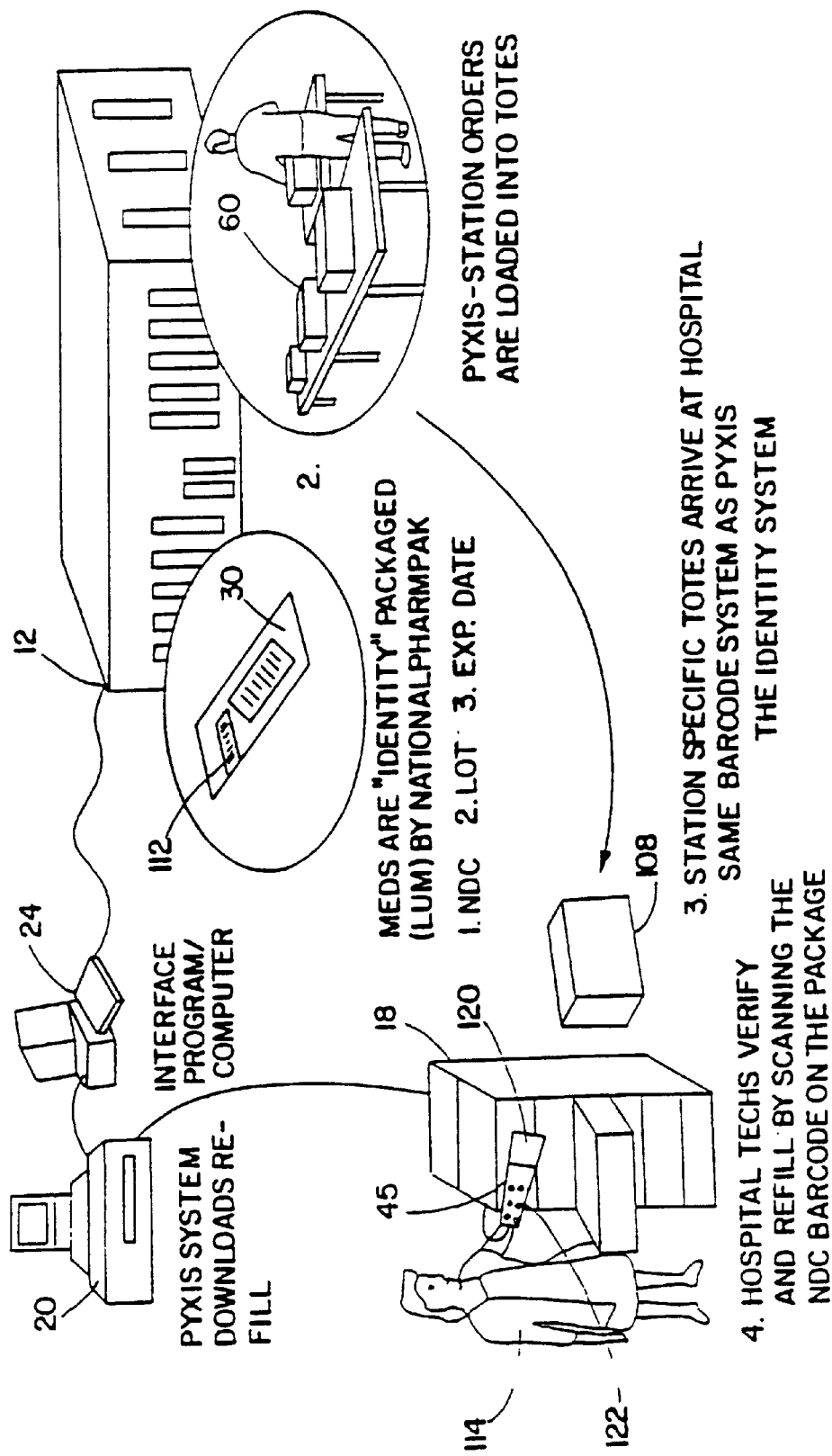
FIG. 7 shows a schematic diagram of a preferred embodiment of the system of the present invention.

Referring to FIG. 7, there is shown a schematic diagram of a preferred embodiment of the present invention. There is shown at 20 a computer in association with a hospital pharmacy. The computer 20 is electronically connected to an interface computer 24. The interface computer 24 is in electronic communication with a computer at a drug supplier or wholesaler 12. The interface computer 24 enables the supplier's computer 12 to receive communications from the hospital pharmacy computer 20.

The hospital pharmacy computer 20 is also in communication with one or more automated drug dispensing machines (DDMs) or stations 18 within the hospital. When a nurse accesses the station 18 to withdraw drugs, the station 18 records the user's name, quantity and type of drug withdrawn, the time of access, and the like. In a preferred embodiment, the nurse will use the drug information collection unit 45 to scan the bar codes on the drug packages removed from the station 18, thereby enabling the station 18 and the pharmacy computer 20 to accurately record and track the dispensed drugs. This information may be conveyed from time to time from the station 18 to the pharmacy computer 20. In this manner, the pharmacy computer 20 is able to know the quantity and variety of all drugs stored in every drug dispensing station 18 in the hospital on any given day. By providing predetermined minimum threshold drug quantity amounts to a database in association with pharmacy computer 20, pharmacy computer 20 may automatically compare the drug quantities existing at each station 18 and if the existing quantities of a particular drug fall below the minimum threshold amount for that drug, the pharmacy computer 20 may place an electronic purchase order with the supplier 12.

When the supplier 12 receives a purchase order from a hospital, the ordered drugs are loaded into totes 60 to be delivered to the hospital. A tote 60 may contain a plurality of unit dose packages 50 of ordered drugs. These unit doses packages 50 may be in packages 30 having a bar code 112 containing information regarding the enclosed drug placed thereon. When the tote 60 arrives at the hospital a hospital technician 114 may scan the bar code 112 on each package 50 with a drug information collection unit 45 as the drug packages are unloaded into either a hospital pharmacy storage facility or directly into a dispensing station 18. If regulatory approval is granted due in part by the accuracy from using bar codes, it may be possible that the drugs could go directly from the DCC 12 to the DDMs 18 at the hospital without having to be checked by a hospital pharmacist. A technician could load the DDMs 18 by scanning the packages 30 of drugs with the drug information collection unit 45 which may be attached to the DDM 18 via hardwire or RF communication. This would be a big time and cost savings. After the drug information collection unit 45 communicates the item ID to the DDM 18, the DDM 18 determines the "hungriest" pocket (discussed below). The technician doing the refill of the DDM 18 does not need to know which specific pocket, drawer, etc. in the DDM 18 contains the item. The DDM 18 tells or shows the technician where to put the item and the technician scans the package 30 and confirms how many packages 30 are loaded into the DDM 18. The location of the packages 30 being stored and the location of the drugs and supplies received at the hospital are known and tracked by the present invention. The drug information collection unit 45 is preferably adapted to port with the system, thus enabling the unit 45 to electronically download its collected and stored information to the pharmacy computer 20. This is discussed in more detail below.

Figure 8:
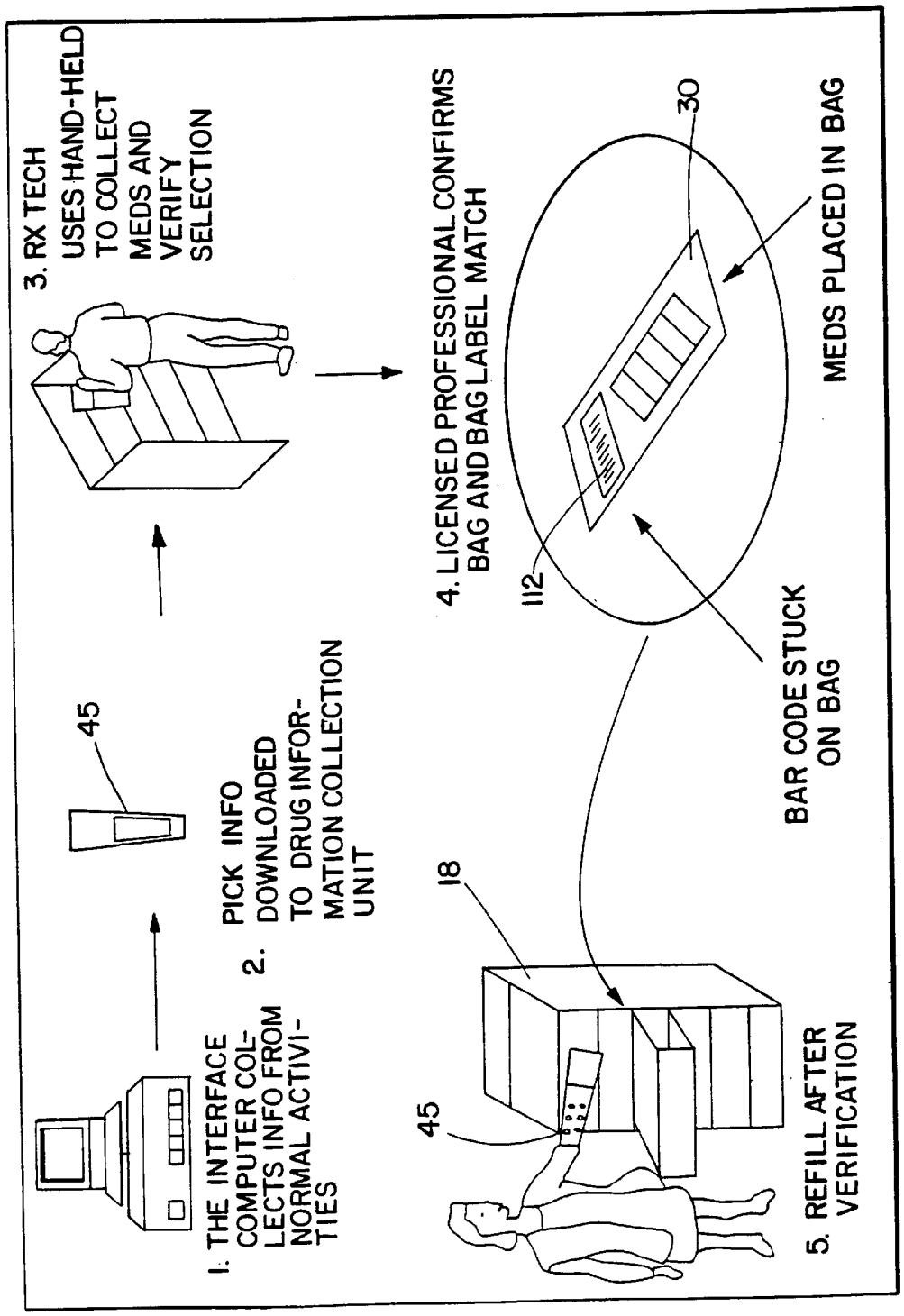
FIG. 8 shows a schematic diagram of a preferred embodiment of the system of the present invention.

Referring to FIG. 8, another embodiment of the invention is shown. In this embodiment a hospital may order its drugs in bulk shipments and/or unlabeled unit dose packages, and later provide its own bar code labels to individual packages for the drugs.

Figure 10:
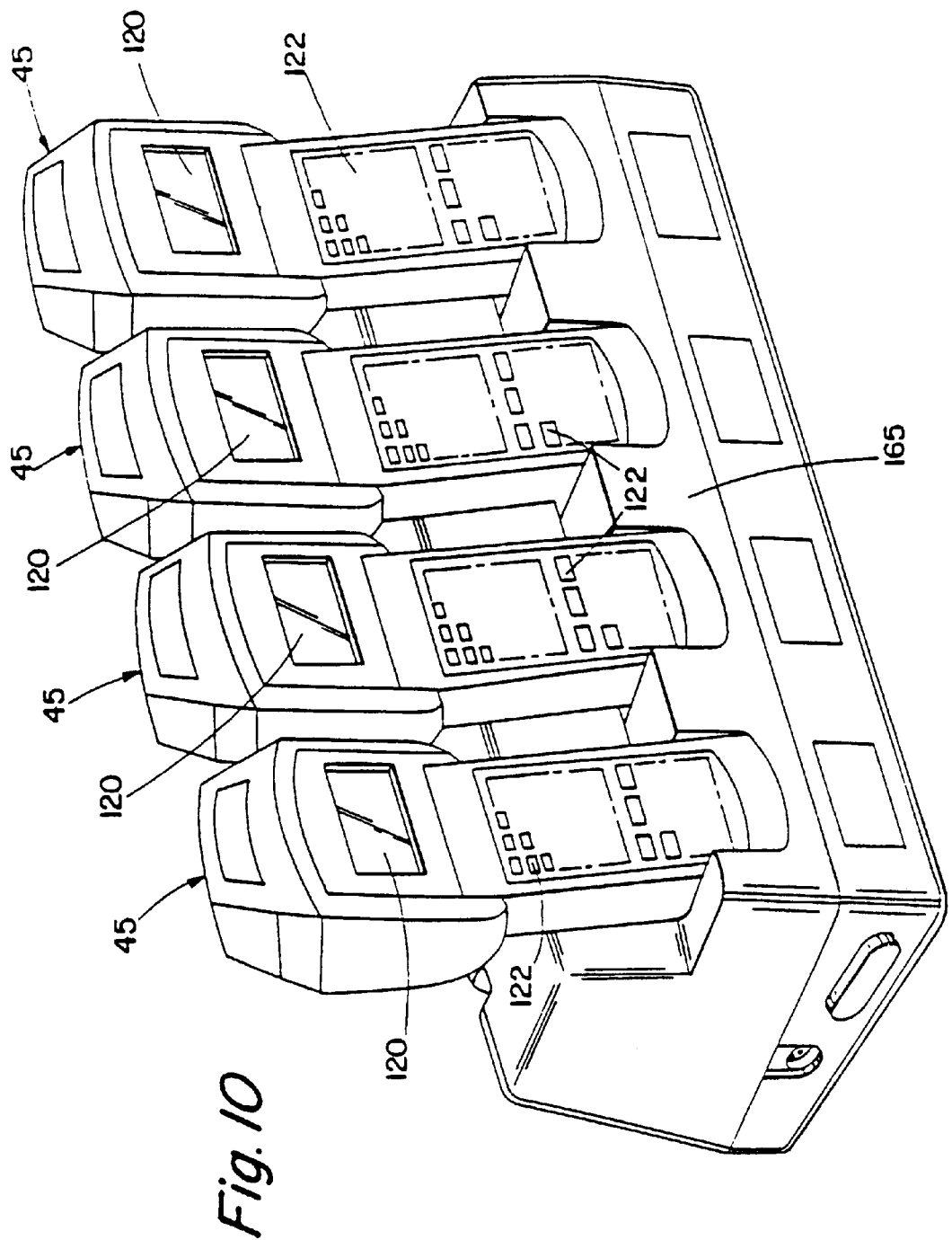
FIG. 10 shows hand held drug information collection units in a recharging cradle in accordance with the present invention.

One type of drug information collection unit 45 that may be used in the present invention is a PDT3 100 that is manufactured by Symbol Technology located in Bohemian, N.Y. FIG. 10 shows the drug information collection units 45 in a recharging cradle 165. Thus, with the system 10 of the present invention, the drug information collection units 45 may be used to help: (1) "pick" drugs from a pharmacy supply within the hospital to deliver to nursing stations; (2) "check" drugs that have been picked and bagged (put in package 30) from a hospital pharmacy supply (the drugs may also be visually checked to confirm that the label matches exactly what is in the package 30 (drug, dose, strength, quantity, packaging integrity, expiration date, etc.))—one goal of getting items from the DCC 12 is to eliminate the pick and check activities of the pharmacy; (3) "deliver" unit dose packaged drugs directly to a dispensing station 18; and/or (4) record unit dose drugs that are dispensed from a dispensing station 18. Each drug information collection unit 45 may be temporarily ported or connected to a dispensing station 18 to download data collected and stored at that station 18. As is known in the art, stations 18 have a computer memory for recording particular types and quantities of drugs stored at that station 18. This information may be downloaded to a drug information collection unit 45.

One goal of the present invention is to standardize the machine replenishment procedure of items (drugs, supplies, etc.) so that the process of putting away items in a machine is the same regardless of whether the items came from the in-house pharmacy or from an outside distributor. The processes of the present invention include: (1) preparing items in the pharmacy or at the drug distribution center 12 for servicing a station 18, including (a) picking items from storage and placing them in the packages 30 to which a bar coded label is attached that identifies the contents of the package 30; and (b) checking that the bar coded label on the bag or package 30 accurately represents the contents of the package 30 and that the contents are suitable for use in the station 18 ("suitable" means that the packaging is intact, item is not out of date, or otherwise unfit for its intended use); (2) receiving pre-prepared items from a distribution center in station specific totes; and (3) delivering bagged/packaged items from the pharmacy or directly from a distributor to the correct pocket in a DDM 18.

Figure 9:
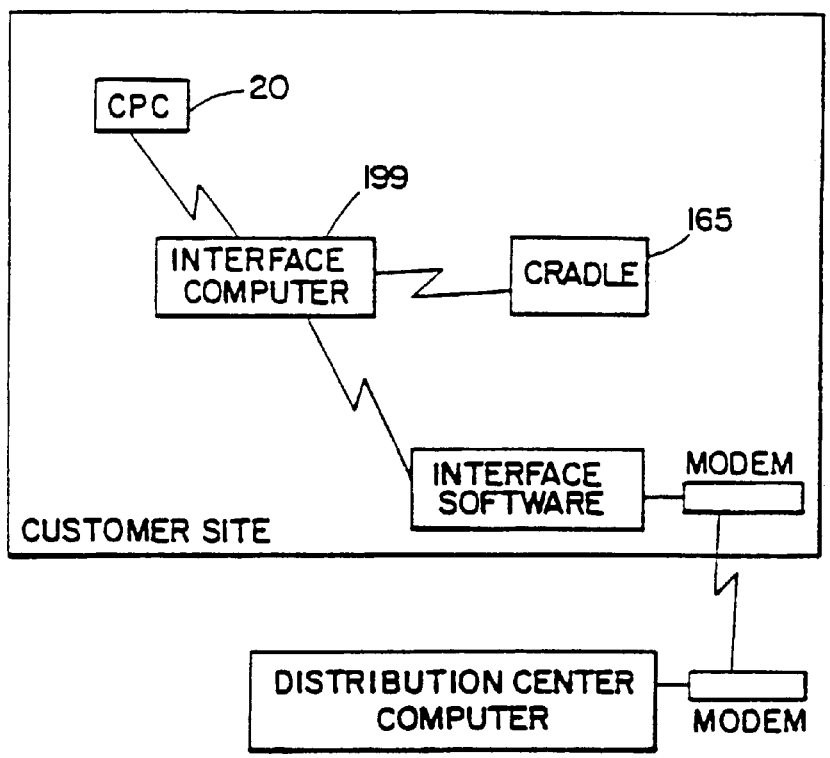
FIG. 9 shows a schematic diagram of a preferred embodiment of the system of the present invention.

Some of the hardware of a preferred embodiment of the system 10 of the present invention in FIG. 9 includes: (1) interface computer 199—a PC that provides an interface to the drug information collection units 45 for current drug dispensing stations 18 and legacy drug dispensing stations 18; (2) drug information collection unit 45—a personal data terminal for directing and recording the pick activity and for recording the check and delivery activities. The drug information collection unit 45 communicates to the interface computer 199 by means of a recharging cradle 165. It may be used in lieu of the station screen and keyboard for performing delivery and unload activities at the station 18; and (3) portable printer that can be connected to the drug information collection unit 45 for printing the various labels needed for the system 10.

Figure 11:
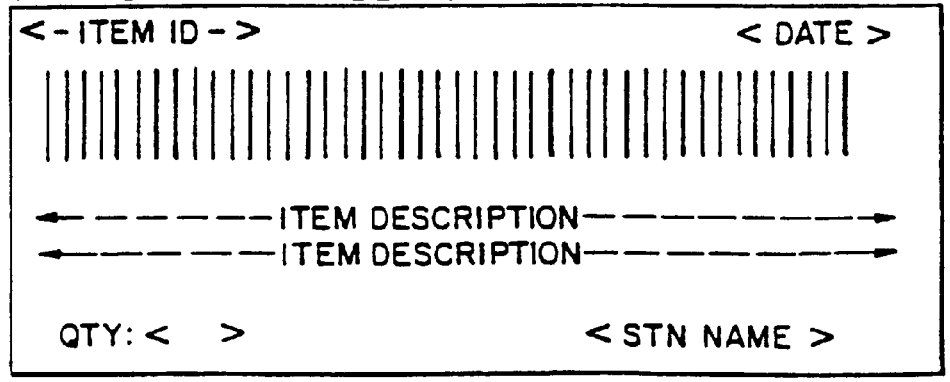
FIG. 11 shows an example of a bag/package label in accordance with the present invention.

The following labels are used in the system 10 and are produceable on the portable printer: (1) shelf labels to identify shelf stock for the picking process; (2) bag/package labels to identify items in the checking and delivery processes; (3) user ID labels for identifying the users of the system 10; and as a recover option, (4) pocket labels to replaced those damaged in machine operation (Pocket labels are installed on certain drawer inserts of the stations 18. Sheets of pre-printed pocket labels are provided for configurable pockets in the drawers of the stations 18.). Examples of these labels are shown in FIGS. 11–13.

In a preferred embodiment, the bar coding generated by the system 10 is code 128. The drug information collection unit 45 preferably is configured to read code 128 and UPC-A for packages 30 from the distribution center. Station pocket inventory is maintained on the CPC 20 from pocket access messages from the various stations 1S. This information is shared by the CPC 20 with the interface computer 199 in real time mode. At configured times, the interface computer 199 creates a database of station pocket needs as a subset of this inventory information. This database of station pocket needs is uploaded to the drug information collection unit 45 based upon the date/time of the last snapshot and drug information collection unit 45 activity. The drug information collection unit 45 directs activities and validates entered information based upon this snapshot database.

In a preferred embodiment, drug information collection unit-directed picking starts with the operator logging onto the drug information collection unit 45 and identifying: (1) the stations 18 to be serviced, either by zone or by station name; (2) the storage areas from which items are to be picked for servicing the stations 18; and (3) the order that item will be picked, either items by station, or stations by item. From this point, the drug information collection unit 45 presents sequentially to the operator the name and ID of an item to be picked, the station 18 for which it is to be picked and the area from which it is to be picked. After scanning the shelf label associated with the identified item and confirming quantity picked, the drug information collection unit 45 may print a bag/package label to identify the items in the bag/package 30.

For out-of-stock conditions or other ad hoc picking, operator-directed picking is possible. This starts with the operator logging onto the drug information collection unit 45 and identifying the station 18 to be serviced. The operator then goes to the desired pick area and scans a shelf tag and completes the picking activity as described above. After completing all picking activity, the drug information collection unit 45 is place into the cradle 165 and all pick activity records are uploaded to the interface computer 199 for future reporting.

Once packaged and labeled, the package 30 and the items in the package 30 are viewed as being owned by the label. This facilitates reorganization of packages 30 to be delivered or checked such that any operator with any drug information collection unit 45 can complete an evolution by using the bar-coded information. A drug information collection unit 45 is then used to capture the check process either accepting or rejecting the package 30 of picked items. The procedure involves physical inspection of the package 30 and its label to determine whether or not the items match the label and the items are suitable for delivery. Then the operator uses the default package 30 status of acceptable or selects a reason identifying a problem and scans the bag/package label. The only unsatisfactory reason that does not result in the pick being voided may be quantity discrepancy. For quantity discrepancy, the operator is preferably allowed to enter the correct quantity and generate a corrected bag/package label. Any other discrepancy recorded by scanning the bag/package label preferably voids the pick. After completing the check activity, the drug information collection unit 45 is placed into the cradle 165 to upload all activity records to the interface computer 199 for future reporting.

Linked to the station 18 by a serial connection, the drug information collection unit 45 acts as a remote monitor and keyboard. The station 18 controls who has access to the items in the station 18 based upon existing user authorization. After connecting the drug information collection unit 45 to the station 18, the user logs onto the station 18. The user then selects a package 30 and scans the label. From the perspective of the operator, it makes no difference whether the bag/package 30 was packed in the pharmacy or at the supplier distribution center. The procedure is preferably the same regardless.

The label information is communicated to the station 18 which then determines the "hungriest pocket." Hungriest pocket is defined as (1) empty or (2) if the item is in more than one pocket, the pocket wherein the difference of maximum to current quantities is greatest. Once the hungriest pocket is determined, the station 18 causes the drawer with the hungriest pocket to open. Once the station 18 opens a drawer the operator is prompted to scan the pocket label to confirm that the destination has been identified. Depending on station configuration which is communicated to the drug information collection unit 45, the operator may be prompted for the beginning pocket quantity and for the next applicable item expiration date. The operator then confirms the quantity being put away and then completes the delivery. The activity in the pocket is communicated to the CPC 20 by the station 18 and by the CPC 20 to the interface computer 199 and then all information is available for reporting by the interface computer 199. In another embodiment, one platform may be used that performs all of the functions of the interface computer 199 and the CPC 20 in one unit. Another embodiment may have the combined functions of the interface computer 199 and the CPC 20 in the DDMs 18, so the DDMs 18 communicate directly to the DCC 12 (as well as to other computers in the hospital).

With a drug information collection unit 45 connected to a station 18, and with the station 18 in electronic communication with pharmacy computer 20, stocking messages may be sent to the user via a display 120 on the drug information collection unit 45. When a user scans a bar code on a package the station 18 may acknowledge this collected data and inform the user via an electronic message displayed on the display panel 120 where (i.e., which drawer and pocket) to place that particular package of drugs. The user may confirm the quantity of drugs in that drawer before adding additional drugs to the drawer and may enter the preexisting quantity into the drug information collection unit 45 via keypad 122. In the same manner the user 114 may enter the quantity of drugs added to a drawer. This process may be repeated until the station 18 is entirely replenished.

Bag/Package Label

The bag/package printed during the picking activity in the pharmacy preferably contains in bar code form the local item identifier, the picked quantity, and the picked serial number. The bar code uses a data identifier to differentiate this bar code from any other kind. The information in the bar code is delimited by the | (ASCII pipe) character. An example of a bag/package label is shown in FIG. 11.

Communication: POL/SELECT Protocol

The drug information collection unit 45 communicates with the interface computer 199 and with the station 18 using the POL/SELECT protocol. This method is designed to manage multiple terminals on a single asynchronous communications line. Although the protocol provides for downloading to multiple terminals, restrictions of the cradle 165 and drug information collection unit 45 architecture limit communication to only a single device at a time. This protocol is preferably able to grow with this feature set to be usable with RF communication.

The interface computer 199 assigns addresses to the drug information collection units 45 and maintains a permanent list of those assigned addresses. Using these addresses, the interface computer 199 is able to send and receive blocks of data and files to each terminal while maintaining a separate status condition for each terminal. The interface computer 199 manages the addresses.

The type of message blocks handled by the protocol are POL and SEL. Acknowledgment, ACK, and negative acknowledgment NAK are used as part of the exchange. The following description provides detail:

POL/SELECT: The POL Sequences.

NEW ADDRESS POL

The New Address POL sequence is designed to assign an address to a drug information collection unit 45 that has not received one or has lost its address. This POL is ignored by drug information collection units 45 that have an assigned address. The interface computer 199 sends a New Address POL at the start of each cycle. A drug information collection unit 45 needing an address responds to the New Address POL with a DataBlock containing its own minutes and seconds (mmss) at that moment in time. When the interface computer 199 receives the DataBlock, it confirms with a DataACK. When the drug information collection unit 45 receives the confirmation DataAck, the drug information collection unit 45 again responds with another DataBlock containing its then current minutes and seconds (mmss). The interface computer 199 confirms this second DataBlock with a DataAck. This double confirmation process is designed to take advantage of the fact that only one drug information collection unit 45 will be granted access to the cradle-guarded serial line, and the second DataBlock-DataAck sequence is possible only with the one drug information collection unit 45 that wins access to the serial line.

The interface computer 199 will not consider the address assigned if there is any break in this discipline. The terminal must wait for another New Address POL. Following is a sample exchange between the interface computer 199 and a drug information collection unit 45 to be assigned the next ID in sequence "Rv".

| interface computer 199 | Terminal |
| --- | --- |
| EOT/POL to 00 → | |
| | ← "R" Data Block containing mm:ss from drug information collection unit 45 |
| DataAck to Rv → | |
| | ← Rv sends "R" Data Block containing <new mm:ss> |
| DataAck to Rv → | |
| | drug information collection unit 45 adopts new address |
| Add address to assigned address list | |

GENERAL POL

This general POL sequence is designed to provide a device with the means to determine the address of the drug information collection unit 45 in communication with it. The device may be the interface computer 199 or the station 18. The interface computer 199 will send a general POL and will wait a predefined period of time for a terminal response. The time is set by SEC_WAIT_FOR_ACK in PROCAR.INI. The drug information collection units 45 in the cradle 165 will bid for the communication line. The drug information collection unit 45 who has the comm line will wait to be polled for 30 seconds before relinquishing the line to another drug information collection unit 45. When a general POL is received the drug information collection unit 45 who has the comm line will respond with an NAK if it does not have data to upload or a Data Block if it has data for the host. When the interface computer 199 receives a Data Block, it confirms with a dataACK. If the interface computer 199 has data to send the drug information collection unit 45, it continues with a specific SEL sequence. After successfiully communicating with the interface computer 199 the drug information collection unit 45 will sleep for two minutes.

The following is a sample exchange between a interface computer 199 and drug information collection unit 45 with ID AB.

| Host | Terminal |
| --- | --- |
| POL to 11 → | |
| | ← AB sends data block "P" or "C" terminated with ETX (more to follow) |
| (BCC is OK) DataACK to AB → | |
| | ← AB sends data block terminated with EOT (no more to follow) |
| (BCC is bad) NAK to AB → | |
| | ← AB resends data block terminated with EOT (no more to follow) |
| (BCC is OK) DataACK to AB → | |
| | (no response) |

At the station 18, the station 18 periodically issues a general POL and waits a defined period of time for drug information collection unit 45 response. If there is no response, the POL times out and it is assumed that there is no drug information collection unit 45 connected. If there is a drug information collection unit 45 attached, the drug information collection unit 45 responds with a data block that containing its IID address. From the receipt of drug information collection unit 45 response, the station 18 may initiate a specific POL/SEL sequence as required.

The following is a sample exchange between a station 18 and drug information collection unit 45 with ID HK:

| Station | Terminal |
| --- | --- |
| POL to 11 → | |
| | ← HK sends ACK with ID |
| EOT/POL to HK → | |
| | ← HK sends NAK (nothing to send) |

POL/SELECT: The SEL Sequences.

SPECIFIC SEL

The specific SEL sequence is designed to ask a specific drug information collection unit 45 if it is ready to receive data from the host. If the drug information collection unit 45 has no data to send, and is ready to accept data, it responds with an ACK. The host responds with the first of 'n' number of data blocks to the drug information collection unit 45. Each intermediate block is terminated with an ETX. The last data block of the set terminates with an EOT. If the drug information collection unit 45 has data to send, it responds with a NAK. The host responds to the NAK with a specific POL to initiate the transfer of information from the drug information collection unit 45. Upon completion of this transfer, the host repeats the Specific SEL. This allows the drug information collection unit 45 to upload any information it contains before receiving an updated database.The basic concept is that the drug information collection unit 45 upload activity records to the host before new information is communicated to the drug information collection unit 45 from the host.

The following sequence is a sample exchange between the interface computer 199 and drug information collection unit 45 with ID AO:

| Host | drug information collection unit 45 |
|---|---|
| SEL to AO → | |
| | ← NAK (need to unload first) |
| SEL to AO → | |
| | ← AO sends ACK (ready to receive) |
| Host sends DataBlock terminated with ETX → (more to follow) | |
| | ← DataACK (BCC is OK) |
| Host sends DataBlock terminated with EOT → (no more to follow) | |
| | ← DataACK (BCC is OK) |
| SEL to AO → | |
| | ← AO sends ACK (ready to receive) |
| Host sends DataBlock terminated with EOT → (no more to follow) | |
| | ← ACK (BCC is OK) |

POL/SELECT: Glossary
ACK (also see DataACK)
Positive acknowledgment to non-data blocks.

| Character | Hex | Description |
|---|---|---|
| SOH | 01 | start of header |
| ADR | | two character drug information collection unit 45 Address (ID) |
| ACK | 06 | positive acknowledgment character |
| EOT | 04 | end of transmission character |
| BCC | | block check character |

In response to a Specific SEL, it indicates that no data needs to be sent from the drug information collection unit 45 before receiving from the host.

ADR—See drug information collection unit 45 address.

BCC—The BCC is a 3-character block check that is calculated by using every character from the first address character through the ENQ/ETX/EOT character, inclusive. The only characters not included are the SOH and the BCC itself It is calculated by initializing an int to zero and successively using exclusive-or on every character into this int. The three-digit ASCII representation of this integer is the BCC.

BlkNbr—Block number field.

If the block number is 0 (zero), and the FLAG is "A" or "B", the block contains a file name and file size for a file that will be subsequently transmitted. The data field is formatted "<fname>|<fsize>". <fname> is the name of the file and <fsize> is the size of the file. The name is in ASCII (non binary) format, and the size is in ASCII digits. The values are delimited by an ASCII pipe (|).

If the block number is greater than 0 (zero), and the FLAG is "A", the data field contains the indicated block of data for the file being transmitted. The data is in ASCII (non-compressed) format.

If the block number is greater than 0 (zero), and the FLAG is "B", the data field contains the indicated block of data for the file being transmitted. The data is in compressed (binary) format. In binary data blocks, embedded ESC/ETX/EOT characters are transmitted with a leading ESC character. For example, an embedded ESC character would be transmitted ESCESC. This allows the trailing ETX/EOT characters to be distinguishable from embedded ETX/EOT characters.

DataACK (also see ACK)—Positive acknowledgment to DataBlocks. Provides confirmation of receiving the Dat-aBlock number contained in the text field.

| Character | Hex | Description |
|---|---|---|
| SOH | 01 | start of header |
| ADR | | two character PDT Address (ID) |
| ACK | 06 | positive acknowledgment character |
| STX | 02 | start of text character |
| BlkNbr | | 5 ASCII digit block number of last block received correctly |
| EOT | 04 | end of transmission character |
| BCC | | block check character |

Data Block—Expected order of data and delimiters in a data block.

| Character | Hex | Description |
|---|---|---|
| SOH | 01 | start of header |
| ADR | | PDT Address (ID) |
| FLAG | | flag |
| BlkNbr | | 5 ASCII digit block number |
| Separator Character | 7C | Separates BlkNbr from BlkSz |
| BlkSz | | 5 ASCII digit block size - data portion only |
| STX | 02 | start of binary text field |
| Data | | variable length data. If the FLAG = B, the data is binary, otherwise its ASCII. |
| ETX/EOT | | end of text/end of transmission |
| BCC | | block check character |

If the FLAG is "B", then the data is binary. In binary data transmissions, the first block, block number zero, will contain the filename, file size and block size. They will be in ASCII format following the STX as follows: "STX<filename>|<filesize>|<blocksize>ETX". The "<" and ">" are not included. The block size is the size of the data block only; the characters between STX and ETX. The ETX/IBCC position is determined by calculation only. It will be BlkSz characters from the first data character. There is no other way to differentiate between embedded control characters and the ending control character.

ENQ—Hex value of 0x05. The ENQ character indicates the end of a POL block, or the end of a SEL block. It is followed immediately with the BCC.

EOT—End of transmission character. Hex value of 0x04. It is transmitted by the host to reset all drug information collection units 45 to idle receive state. Immediately precedes POL and SEL blocks. It is also used to terminate data blocks when there is no more data to follow.

ETX—End of text character. Hex value of 0x03. It terminates a data block when there are more data blocks to follow.

FLAG—One ASCII alphabetic character providing information concerning the nature of the data block.

| Character | Description |
|---|---|
| A | Indicates an ASCII file is being transmitted. |
| B | Indicates a binary file is being transmitted. |
| C | Check record being uploaded from a drug information collection unit 45. Format: "itemId|pickSerial|checkedQty| checkedTm(ASCII)|checkerId|loadOrRefill|checkStat|". |

-continued

| Character | Description |
|---|---|
| D | Indicates a non-file data block. |
| I | Identification block. |
| L | Request from a drug information collection unit 45 to be downloaded now. |
| P | Pick record being uploaded from a drug information collection unit 45. Format: "stnName\|pickSerial\|pickedQty\|pickedTm(ASCII)\|pickerId\|loadOrRefill\|". |
| R | Address acceptance. Format: "mm:ss". drug information collection unit 45's minutes and seconds. |
| S | Station data block. Message contains unique message number to identify contents and format. |

Max Block Size—Two character ASCH number indicating a power-of-2 maximum block size. For example; 07=2 to the power of 7, or 128.; 12=2 to the power of 12, or 4096. This allows the host to dynamically set the optimum maximum block size. The actual block size is variable within the maximum limit. Stations 18 will probably use a small max block size and the interface computer 199 will probably use a larger maximum to facilitate large file transfers.

NAK—Negative acknowledgment. Hex value of 0×15. Single-character response by both the host and drug information collection unit 45 to a data block received with a bad BCC. In response to a specific SEL, it is sent by a drug information collection unit 45 to indicate that it is not ready to receive information from the host.

NewAdr—Used in the New Address POL, the next available address for a drug information collection unit 45 not yet IDed.

POL—In the specific POL, it is a method used by the host to control which drug information collection unit 45 is queried for information to be sent to the host. In the General POL, it is a method used by a station 18 to determine whether or not a drug information collection unit 45 is attached to the station 18 and the identity of that drug information collection unit 45. In the New Address POL, it is a method used by the interface computer 199 to identify drug information collection units 45 needing an address to be assigned. The following is the POL block definition.

| Character | Hex | Description |
|---|---|---|
| EOT | 04 | Resets all drug information collection units 45 to receive idle state |
| ADR | | drug information collection unit 45 address (Id). Two ASCII alpha characters. ADR "00" means its a NewAddress POL. ADR "11" means its a General POL. |
| POL | 70 | Asks if drug information collection unit 45 has something to send |
| TIME | | MMDDYYHHMMSS. Allows drug information collection units 45 to synchronize time |
| Either [NewAdr] or [MaxBlkSz] | | 2 ASCII digits. If NewAdr POL - Next available drug information collection unit 45 address. If not NewAdr POL - Maximum data block size |
| ENQ | 05 | End of POL block. |
| BCC | | Block Check Character. |

SEL—In the specific SEL, it is a method used by the host to notify a specific drug information collection unit 45 that the host has data to transmit to the drug information collection unit 45. If the drug information collection unit 45 has data to transmit to the host, the drug information collection unit 45 should respond with a NAK, otherwise the drug information collection unit 45 should respond with an ACK. The following is the SEL block definition.

| Character | Hex | Description |
|---|---|---|
| EOT | 04 | Resets all drug information collection units 45 to receive idle state |
| ADR | | drug information collection unit 45 address (Id). Two ASCII alpha characters. |
| SEL | 71 | Asks if drug information collection unit 45 is ready to receive. |
| TIME | | MMDDYYHHMMSS. |
| MaxBlkSz | | 2 ASCII digit maximum block size. |
| ENQ | 05 | End of SEL block. |
| BCC | | Block Check Character. |

Drug information collection unit address—Two-character address used to uniquely identify a specific drug information collection unit 45. The address consists of two ASCII characters sequentially assigned from the ranges of A–Z and a–z. This provides 2,704 unique addresses (52×52). It is assigned, and tracked by the interface computer 199, to a drug information collection unit 45 using a New Address POL. Once assigned, the drug information collection unit 45 should remember its ADR forever.

Special-purpose numeric addresses are reserved.
00 New Address POL.
11 General POL.

Drug Information Collection Unit Data
Data Business Rules

Each drug information collection unit 45 may be inserted into one of several daisy-chained cradles 165 for recharging and receiving periodic downloads. (The download frequency is configurable in minutes in the PROCAR.INI, default of 60, minimum of 10.) They also, on being re-cradled, upload activity records to the interface computer 199. The relationship between the interface computer 199 and the cradled drug information collection units 45 is peer-to-peer. Communication is accomplished using a Y-modem protocol with some variation for efficiency. The downloaded picklist goes stale in 4 hours restricting an operator from picking against the stale list. Unless specified otherwise, the lines containing item name text are displayed in reverse video.

The drug information collection unit 45 receives the current time from the interface computer 199 whenever data is exchanged between the devices. This reinforces the drug information collection unit 45 uses the correct time stamp as it records user activities. When a drug information collection unit 45 is first introduced to the system 10, it receives from the interface computer 199 a unique identifier to be used in serializing pick activities. This identifier is a 2 character base 62 value represented by ASCII values 0 through 9, A through Z, and a through z. The drug information collection unit 45 appends to this identifier a sequence number which it increments and maintains also in base 62. The 4 characters are used to track activity and eventually reconcile pick activities to check activities to delivery activities. Should a drug information collection unit 45 be transferred to a new site after use at a previous site, this identifier should be cleared in order to ensure it gets a new identifier unique to its new environment.

Interface Computer: Reports
Hand-Held Reconciliation Report
A. Not Checked and Not Delivered This report is sorted by Class, Station, Item Description. It presents an accounting of items that were picked but got no further in the replenishment process.

B. Checked But Not Delivered

This report is sorted by Class, Station, Item Description. It presents an accounting of items that were picked and checked but never delivered to a station 18. It does not include picks that were checked and as a result the label was voided.

C Not Checked but Delivered

This report is sorted by Station, Item Description, Deliverer ID. It presents an accounting of items that were picked but not checked before delivery to a station 18. The interface computer 199 can turn off this report of account agrees no check is required.

Checking Reports

If the check reporting is disabled for this customer site in PROCAR.INI file, delivered date/time and deliverer ID is used in lieu of check date/time and checker ID.Errors Caught in Checking This report is sorted by picker ID and item description. Error categories are patterned after the screen options.

Checking Detail

This report is sorted by station 18, item description, and item ID. If checking is disabled in PROCAR.INI, delivery information is substituted for checking information.

Having described the invention in detail, those skilled in the art will appreciate that, given the present disclosure, modifications may be made to the invention without departing from the spirit of the inventive concept herein described. Therefore, it is not intended that the scope of the invention be limited to the specific and preferred embodiments illustrated and described. Rather, it is intended that the scope of the invention be determined by the appended claims.

What is claimed is:

1. A system for drug distribution comprising:
   a package containing at least one drug, said package further including information thereon relative to said drug;
   a computer at a health care provider, said computer adapted for storing said drug information and maintaining drug counts;
   an automated drug dispensing machine at a location at the health care provider, said automated drug dispensing machine in electronic communication with said computer;
   one or more drug information collection units adapted to obtain drug information from said package, said drug information collection units adapted to communicate the drug information to said computer;
   whereas said system, including said computer, said automated drug dispensing machine, and said drug information collection units, records drugs received by said health care provider, records drugs dispensed to patients at said health care provider, and records an ongoing inventory of drugs stored at said health care provider;
   wherein said automated drug dispensing machine comprises a cabinet including a plurality of drawers with pockets wherein each pocket holds a particular type of drug and wherein said cabinet electronically controls access to each of said drawers.

2. The system of claim 1 wherein said first computer maintains a master database, monitors times of system activities and transactions, generates reports of system activities and transactions, and manages the system activities and transactions, including the drugs loaded in, stored in, and dispensed by said drug dispensing machines.

3. The system of claim 1, wherein said drug package includes a bar code containing drug information relative to said drug in said package.

4. The system of claim 3 wherein said bar code includes information pertaining to the drug manufacturer's lot number from which the drug within said package was obtained, the NDC of the drug within said package, the expiration date of the drug within said package, and the type of drugs within said package.

5. The system of claim 1, wherein one or more of said drug information collection units is a hand held unit.

6. The system of claim 3 wherein one or more of said drug information collection units is in electronic communication with one or more of said drug dispensing machines, said drug information collection unit being in electronic communication with said computer and said drug information collection unit being adapted to scan said bar codes on said packages and communicate the information obtained from said bar codes to said computer and to said drug dispensing machines.

7. The system of claim 6 wherein said automated drug dispensing machine comprises a cabinet including a plurality of drawers with pockets wherein each pocket holds a particular type of drug and wherein said cabinet electronically controls access to each of said drawers, and when said drug dispensing machine needs to be loaded with a drug, a user scans the bar code of a package to be loaded with said drug collection unit and the proper drawer opens and the proper pocket within the drawer to be filled with the drug is indicated to the user.

8. The system of claim 6, wherein when a drug is to be dispensed from said drug dispensing machine, a user scans the bar code of a package to be dispensed with said drug collection unit and information about the user, the dispensed drug, and the patient to receive the dispensed drug is communicated to said computer.

9. The system of claim 1, wherein said system also records information about drugs loaded in each drug dispensing machine, records information about drugs dispensed from each drug dispensing machine, and records the inventory of drugs stored in each drug dispensing machine.

10. The system of claim 1, further including a second package to hold one or more of said first packages therein, said second package being one of the group consisting of a plastic bag, a box, a carton, a card of said first packages, and a bundle of said first packages fastened together.

11. The system of claim 10 wherein said drug package includes a bar code containing drug information relative to said drug in said package and said bar code includes information pertaining to one or more of the group consisting of the drug manufacturer's lot number from which the drug within said package was obtained, the NDC of the drug within said package, the expiration date of the drug within said package, the type of drugs within said package, the dose of the drugs within said package, the size of said package, the number of drugs within said package, and FDA related information regarding the drug within said package.

12. The system of claim 1, further comprising a second computer located at a drug supplier facility, said second computer in electronic communication with said first computer, said second computer being adapted to receive an electronic purchase order from said first computer.

13. The system of claim 12, wherein said second computer is adapted to receive an electronic purchase order from said first computer automatically when said first computer indicates that a quantity of a certain drug in the inventory of said health care provider has fallen below a predetermined threshold amount.

14. The system of claim 12 further including an electronic interface between said first computer and said second computer to enable said first computer and said second computer to electronically communicate and share data with each other.

15. The system of claim 12 wherein said electronic interface is one or more of the group consisting of a modem, an interface computer, a gateway, and interface software running on said first computer and said second computer.

16. The system of claim 15 wherein said interface computer electronically communicates and shares data with said drug information collection units.

17. The system of claim 16 further including a cradle for holding one or more of said drug information collection units, said cradle recharges said drug information collection units and facilitates communication and data sharing between said interface computer and said drug information collection units.

18. The system of claim 15 wherein said interface computer includes a database of system inventory, said database being the source of information for picking/checking reports related to system activity, including order and delivery information of the drugs.

19. The system of claim 12 further including one or more second drug information collection units at the drug supplier facility that are adapted to obtain drug information from said packages, said second drug information collection units being in electronic communication with said second computer being adapted to download collected drug information received by said second drug information collection units and to enter the drug information into said second computer.

20. The system of claim 19 wherein said drug packages include a bar code containing drug information relative to said drug in said packages and said bar code includes information pertaining to one or more of the group consisting of the drug manufacturer's lot number from which the drug within said package was obtained, the NDC of the drug within said package, the expiration date of the drug within said package, the type of drugs within said package, the dose of the drugs within said package, the size of said package, the number of drugs within said package, and FDA related information regarding the drug within said package.

21. The system of claim 1, further comprising a second computer located at a drug supplier facility, said second computer in electronic communication with said drug dispensing machines, said second computer being adapted to receive an electronic purchase order from said drug dispensing machines.

22. The system of claim 12, wherein said second computer tracks the total quantities of drugs shipped to said health care provider and the balance of the quantity of any unshipped drugs purchased by the health care provider.

23. The system of claim 12, wherein said second computer is adapted to produce an invoice to said health care provider for a purchase of said drugs.

24. The system of claim 12, wherein a drug supplier uses said second computer to maintain an inventory of drugs purchased by said health care provider and warehouses said purchased drugs while periodically delivering purchased drugs to said health care provider in accordance with levels of need of said health care provider as indicated by drug inventory management software on said second computer.

25. A system for drug inventory management, said system comprising:
 a first data processor in connection with a drug distribution center;
 a first drug inventory management software program in connection with said first data processor;
 a second data processor in connection with a health care provider;
 a second drug inventory management software program in connection with said second data processor;
 a low unit measure dose package including contents of a particular variety of drug, said package including at least one bar code including information pertaining to one or more of the group consisting of the drug manufacturer's lot number from which the drug within said package was obtained, the NDC of the drug within said package, the expiration date of the drug within said package, the type of drugs within said package, the dose of the drugs within said package, the size of said package, and the number of drugs within said package, whereby the information the size of said package, and the number of drugs within said package, whereby the information gathered from scanning said bar code is entered into said first and said second software programs;
 an interface between said first data processor and said second data processor to facilitate electronic communication and data sharing therebetween;
 a drug information collection unit adapted to obtain drug information from the bar code on said package, said drug information collection unit adapted to electronically communicate the drug information to said first and said second software programs;
 wherein said drug distribution center maintains an inventory of drug purchased by said health care provider and warehouse said purchased drugs at said drug distribution center while periodically delivering purchased drug to said health care provider in accordance with levels of need of said health care provider as indicated by said second drug inventory management software program.

26. The system of claim 25, further comprising:
 a drug dispensing machine at said health care provider, adapted to receive said low unit measure package.

27. The system of claim 25, wherein said drug distribution center software tracks the total low unit measure quantities of drugs shipped to said health care provider and the balance of the quantity of unshipped drugs purchased by the health care provider.

28. The system of claim 25, wherein said distribution center software is adapted to produce an invoice to said health care provider for the purchase of said drugs.

29. The system of claim 25, wherein said first drug management software program in connection with a drug distribution center tracks drugs delivered to said health care provider, in low unit dose measurements.

30. A method for drug distribution to health care providers, said method comprising the steps of:
 providing an automated drug dispensing machine comprising a plurality of drawers wherein access to each of said drawers is controlled;
 providing a first drug inventory management software program in connection with a drug distribution center;
 providing a second drug inventory management software program in connection with a health care provider;
 providing a low unit measure dose packaging including contents of a particular variety of drug;
 applying a bar code onto said packaging, wherein said bar code includes information pertaining to one or more of the group consisting of the drug manufacturer's lot number from which the drug within said package was obtained, the NDC of the drug within said package, the expiration date of the drug within said package, the type of drugs within said package, the dose of the drugs within said package, the size of said package, and the number of drugs within said package;

scanning said bar code with a drug information collection unit to thereby cause data from said bar code to enter at least one of said first program of said second program; and providing a computer interface between said first software program and said second software program to facilitate electronic communication and data sharing there between.

31. A method for drug inventory management, said method comprising the steps of:

providing a package containing at least one drug;

applying a bar code on said package, said bar code including information relative to said drug;

providing a computer at a health care provider, said computer being adapted for storing said drug information and maintaining drug counts;

providing one or more automated drug dispensing machines at a location at the health care provider, said automated drug dispensing machines being in electronic communication with said computer;

scanning said bar code with a drug information collection unit adapted to obtain drug information from said bar code;

communication the drug information from said drug information collection unit to said computer;

whereas said system, including said computer, said automated drug dispensing machines, and said drug information collection unit, records drug received by said health care provider, records drugs dispensed to patients at said health care provider, and records an ongoing inventory of drugs stored at said health care provider; and wherein said automated drug dispensing machine comprises a cabinet including a plurality of drawers with pockets wherein each pocket holds a particular type of drug and wherein said cabinet electronically controls access to each of said drawers.

32. The method of claim 31 wherein said bar code includes information pertaining to one or more of the group consisting of the drug manufacturer's lot number from which the drug within said package was obtained, the NDC of the drug within said package, the expiration date of the drug within said package, the type of drugs within said package, the dose of the drugs within said package, the size of said package, the number of drugs within said package, and FDA related information regarding the drug within said package.

33. The method of claim 31 wherein when said drug dispensing machine needs to be loaded with a drug, a user scans the bar code of a package to be loaded with said drug collection unit and the proper drawer opens and the proper pocket within the drawer to be filled with the drug is indicated to the user.

34. The method of claim 31, wherein when a drug is to be dispensed from said drug dispensing machine, a user scans the bar code of a package to be dispensed with said drug collection unit and information about the user, the dispensed drug, and the patient to receive the dispensed drug is communicated to said computer.

35. The method of claim 31 further including the steps of recording information about drugs loaded in each drug dispensing machine, recording information about drugs dispensed from each drug dispensing machine, and recording the inventory of drugs stored in each drug dispensing machine.

36. The method of claim 31 further including the step of providing a second package to hold one or more of said first packages therein, said second package being one of the group consisting of a plastic bag, a box, a carton, a card of said first packages, and a bundle of said first packages fastened together.

37. The method of claim 36 wherein said second package includes a bar code containing drug information relative to said drug in said package and said bar code includes information pertaining to one or more of the group consisting of the drug manufacturer's lot number from which the drug within said package was obtained, the NDC of the drug within said package, the expiration date of the drug within said package, the type of drugs within said package, the dose of the drugs within said package, the size of said package, the number of drugs within said package, and FDA related information regarding the drug within said package.

38. The method of claim 31 further comprising the step of providing a second computer located at a drug supplier facility, said second computer in electronic communication with said first computer, said second computer being adapted to receive an electronic purchase order from said first computer automatically when said first computer indicates that a quantity of a certain drug in the inventory of said health care provider has fallen below a predetermined threshold amount.

39. The method of claim 38 further comprising the steps of:

picking drugs at the drug supplier facility to fill the purchase order;

sending the ordered drugs to the health care provider; and loading the drugs into the appropriate drug dispensing machines at the health care provider.

40. The method of claim 39 further comprising the step of providing totes in which to send the ordered drugs to the health care provider, said totes having a bar code thereon that has drug information relative to said drugs in said totes and said bar code including information pertaining to one or more of the group consisting of the drug manufacturer's lot number from which the drug within said package was obtained, the NDC of the drug within said package, the expiration date of the drug within said package, the type of drugs within said package, the dose of the drugs within said package, the size of said package, the number of drugs within said package, and the destination of the totes.

41. The method of claim 40 wherein said bar code on said totes includes identification of the specific drug dispensing machine in which the drugs in the tote are to be loaded.

42. The method of claim 39 wherein the step of loading the drugs into the appropriate drug dispensing machines at the health care provider includes a user scanning the bar code of a package containing a drug to be loaded to obtain the drug information relative to the drug, the drug information is sent to a processor in the drug dispensing machine which makes the proper drawer open and the proper pocket within the drawer to be filled with the drug is indicated to the user.

43. The method of claim 42 further including the step applying a bar code in the pockets of the drug dispensing unit, said bar code containing information about the type of drugs that is to be stored in the pocket, and further including the step of scanning the bar code in the pocket of said drug dispensing machine with said drug information collection unit to confirm that the pocket is the correct one to store the type of drug being loaded.

44. The method of claim 39 further including the step of dispensing drugs from said drug dispensing machine that includes a user scanning the bar code of a package to be dispensed with said drug collection unit and information about the user, the dispensed drug, and the patient to receive the dispensed drug is communicated to said computer.

45. The method of claim 38 further including the step of providing an interface computer between said first computer and said second computer to enable said first computer and said second computer to electronically communicate and share data with each other.

46. The method of claim 45 wherein said interface computer electronically communicates and shares data with said drug information collection units.

47. The method of claim 38 further including the step of providing one or more second drug information collection units at the drug supplier facility that are adapted to obtain drug information from said packages, said second drug information collection units being in electronic communication with said second computer being adapted to download collected drug information received by said second drug information collection units and to enter the drug information into said second computer.

48. The method of claim 38 further including the step of using said second computer to track the quantities and types of drugs shipped to the health care provider and the balance of the quantities of any unshipped drugs purchased by the health care provider.

49. A system for health care supply distribution comprising:

a package containing at least one health care supply, said package further including information thereon relative to said supply;

a computer at a health care provider, said computer adapted for storing said supply information and maintaining supply counts;

one or more automated supply dispensing machines at a location at the health care provider, said automated supply dispensing machines comprising a cabinet including a plurality of drawers wherein said cabinet electronically controls access to each of said drawers and wherein said automated supply dispensing machines are in electronic communication with said computer;

one or more supply information collection units adapted to obtain supply information from said package, said supply information collection units adapted to communicate the supply information to said computer;

whereas said system, including said computer, said automated supply dispensing machines, and said supply information collection units, records supplies received by said health care provider, records supplies dispensed to patients at said health care provider, and records an ongoing inventory of supplies stored at said health care provider.

50. The system of claim 49, wherein said bar code includes information pertaining to one or more of the group consisting of the supply manufacturer's lot number from which the supply within said package was obtained, the NDC of the supply within said package, the expiration date of the supply within said package, the type of supplies within said package, the dose of the supplies within said package, the size of said package, and the number of supplies within said package.

51. The system of claim 49, further comprising a second computer located at a supplier facility, said second computer in electronic communication with said first computer, said second computer being adapted to receive an electronic purchase order from said first computer.

* * * * *